US012389845B2

(12) United States Patent
Bracuto et al.

(10) Patent No.: US 12,389,845 B2
(45) Date of Patent: Aug. 19, 2025

(54) 9-LOX5 GENE VARIANT PROVIDING POWDERY MILDEW RESISTANCE

(71) Applicant: RIJK ZWAAN ZAADTEELT EN ZAADHANDEL B.V., De Lier (NL)

(72) Inventors: Valentina Bracuto, De Lier (NL); Emilio Sarria Villada, De Lier (NL); Adrianus Cornelis Koeken, De Lier (NL); Sara Movahedi, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 254 days.

(21) Appl. No.: 17/741,693

(22) Filed: May 11, 2022

(65) Prior Publication Data
US 2022/0322628 A1   Oct. 13, 2022

Related U.S. Application Data

(63) Continuation-in-part of application No. PCT/EP2020/085930, filed on Dec. 14, 2020, which is a continuation-in-part of application No. PCT/EP2019/085169, filed on Dec. 13, 2019.

(51) Int. Cl.
*A01H 5/08*    (2018.01)
*A01H 6/34*    (2018.01)
*C12N 15/82*   (2006.01)

(52) U.S. Cl.
CPC .............. *A01H 5/08* (2013.01); *A01H 6/342* (2018.05); *C12N 15/8282* (2013.01)

(58) Field of Classification Search
None
See application file for complete search history.

(56) References Cited

FOREIGN PATENT DOCUMENTS

KR    2017 0045778 A    4/2017

OTHER PUBLICATIONS

Takamatsu, S. Studies on the evolution and systematics of powdery mildew fungi. J Gen Plant Pathol 84, 422-426 (2018). https://doi.org/10.1007/s10327-018-0805-4 (Year: 2018).*
Nalam, Vamsi J., et al. "Facilitation of Fusarium graminearum infection by 9-lipoxygenases in *Arabidopsis* and wheat." Molecular Plant-Microbe Interactions 28.10 (2015): 1142-1152. (Year: 2015).*
Nalam, Vamsi J., et al. "Root-derived oxylipins promote green peach aphid performance on *Arabidopsis* foliage." The Plant Cell 24.4 (2012): 1643-1653. (Year: 2012).*
Müller, V., et al. "Lipoxygenase activation in peanut seed cultivars resistant and susceptible to Aspergillus parasiticus colonization." Phytopathology 104.12 (2014): 1340-1348. (Year: 2014).*
Żmieńko, Agnieszka, et al. "Copy number polymorphism in plant genomes." Theoretical and applied genetics 127 (2014): 1-18. (Year: 2014).*
Ben-Naim, Yariv, and Yigal Cohen. "Inheritance of resistance to powdery mildew race 1W in watermelon." Phytopathology 105.11 (2015): 1446-1457. (Year: 2015).*
Keskin, Ozlem, et al. "A new, structurally nonredundant, diverse data set of protein-protein interfaces and its implications." Protein Science 13.4 (2004): 1043-1055. (Year: 2004) (Year: 2004).*
Guo, Haiwei H., Juno Choe, and Lawrence A. Loeb. "Protein tolerance to random amino acid change." Proceedings of the National Academy of Sciences 101.25 (2004): 9205-9210. (Year: 2004) (Year: 2004).*
Thornton, Janet M., et al. "From structure to function: approaches and limitations." nature structural biology 7.11 (2000): 991-994. (Year: 2000) (Year: 2000).*
Ben-Namin, Yariv, and Yigal Cohen. "Inheritance of resistance to powdery mildew race 1W in watermelon." Phytopathology 105.11 (2015): 1446-1457. (Year: 2015).*
Database GenPat Accession No. XP_023545376—linoleate 96-lipoxygenase 6-like [*Cucurbita pepo* subsp. *pepo*] Jan. 22, 2018.
Yariv Ben-Naim, et al., Inheritance of Resistance to Powdery Mildew Race 1W in Watermelon, Phytopathology (Nov. 1, 2015) vol. 105, No. 11, p. 1446-1457.
Kwang-Hwan Kim, et al., Major Quantitative Trait Loci and Putative Candidate Genes for Powdery Mildew Resistance and Fruit-Related Traits Revealed by an Intraspecific Genetic Map for Watermelon ( *Citrullus lanatus* var. *lanatus*) PLOS One (Dec. 23, 2015) vol. 10, No. 12, p. 1-18.
V. Muller, et al., Lipoxygenase Activation in Peanut Seed Cultivars Resistant and Susceptible to Aspergillus parasiticus Colonization, Phytopathology (2014) vol. 104, No. 12. p. 1340-1348.
Sang-Keun Oh, et al., Expression of cucumber LOX genes in response to powdery mildew and defense-related signal molecules, Canadian Journal of Plant Science (2014) vol. 94, p. 845-850.
Haiying Zhang, et al.. Sources of Resistance to Race 2WF Powdery Mildew in U.S. Watermelon Plant Introductions, HortScience (Oct. 2011) vol. 46, No. 10, p. 1349-1352.
International Search Report issued Feb. 22, 2021 in Int'l Application No. PCT/EP2020/085930.

* cited by examiner

*Primary Examiner* — Amjad Abraham
*Assistant Examiner* — Kelsey L McWilliams
(74) *Attorney, Agent, or Firm* — Duane Morris LLP; Thomas J. Kowalski

(57) ABSTRACT

The present invention relates to a plant with a copy number variation (CNV) of a 9-LOX5 gene, wherein the CNV has at least 2 copies of a 9-LOX5 gene, wherein the 9-LOX5 gene comprises SEQ ID NO: 1, or a sequence having at least 60% sequence identity to SEQ ID NO: 1, and wherein the presence of the CNV leads to powdery mildew resistance in the plant. The invention further relates to nucleic acid molecules, methods for selecting powdery mildew resistant plants, the plants thus obtained therefrom, and seeds and parts thereof.

20 Claims, 9 Drawing Sheets
Specification includes a Sequence Listing.

Figure 1: 9-LOX5_1

SEQ ID No. 1: 9-LOX5_1 allele – coding sequence
>copy1_CDS

ATGGTTAAAGGGAAAGTTACTTTGTCCAGAAGCAATTGGATCAATAGGCCAAAACTAAAACTTA
CCCTACAACTCATCAGCTCTGTGAAGTGTGATCCATCAATAGGAAAGCAAGGGAAACATGGAAA
GAAAATATACTTGCAAAATGAAGGAGATGCAAATAATGAAGGGGAAGAGTGTTTAGTGTGAG
TTTTGATTGGGATGAAGAGATTGGGAATCCAGGAGCTATCTTGGTAAGAAACAACCATCGTTTTT
CAAGATTCTTCCTCAAATCTATTACTCTTTTTGATCTACCTGCCTTCGGAAACATCCACTT
TGATTGCAACTCTTGGATTCACCCTAATAGACATACATACAGATCATCACATTTTCTT
TGTAAATAAGGCATATCTTCCTCATGAGACACCAGAGCCACTTCAAAATTATAGAGAGAA
AGAACTCGAAAAAAGAGAGGAGATGGTAGAAGAGTGCCTAAAAATTGGGAAAACATATA
CGACTATGATGTCTACAATGATATTAGTGATTTAGATTCTAATTCAACAAATAAACCCCC
TATTCTTGGAGGATTGGTGCCTTATCCACGTAGAGGAAGAACTGGACGACCACGCTCAAA
AAAAGATGATAGATATGAGACCAGATGTGCAATCAAAGATGTTTATGTTCCCAGTGATGA
AAGATTTAGTGACTTGAAGAAATCAGATTTTGATATTCATGGATTAAGATCAGTGCTTCG
AGACATTAAAGATAAACTTAAAGCTTCATTAGGAAAATCTCCTAAAAGATTGGAGTCTCT
TAAAGATGTGTATGCAATCTATGAACCACGTTCCTTCTTTCGACGAGGGAAATTTCTAAT
GCCCCAGGTGATCGAAGGTAATAAATCTGGATGGAGGACTGATGAAGAGTTCGCTAGAGA
AATGTTGGCAGGAGTAAATCCTATGGTCATTCGTCGTCTCCAAAGTTTCCCACCGACTAG
CAACCTTAACCCTAGTGATTATGGTGATCAAAACAGCAAGATAACACCAAAACAGATTAT
GAATGGTATGGAGGGACTTACGGTAGACCAGGCAATTGCAGAAAACAAGCTGTACATATT
AGATCACCATGATTTAATAATTCCATATCTTAAAAGAATAAATACAACTTCCACAAAAAC
TTATGCTACAAGAACACTTCTCTTCCTAAAAAATGATGGGACTTTGAAGCCTTTAGCAAT
TGAATTGAGCTTGCCACACCCTCAAGGATACCAATTTGGAGCCATTAGTAAAATATTGTT
GCCAGACAAAGGAAGAATTGGGGAACCACTTTGGCAACTAGCTAAAGCTTATGTTGTTGT
CAATGACTCTGGTCACCATCAACTCATCAGCCACTGGCTAAACACACATGCCGTAATTGA
GCCATTTGTGATTGCAACACATAGACAACTCAGTGTTGTTCATCCGATTCACAAGTTGCT
TGTTCCTCACTTTCGATACACCATGAAGATCAATGCTCTTGCAAGATCAACCCTCATTAA
TACTGATGGTATTATTGAGAAAACTCAATATCCTTCTAAGTATTCATGGAGATGTCTTC
TTTTGCTTATCAAAATTGGACTTTACTCAACAAGCACTCCCTGCTGACCTAATCAAGAG
AGGAATTGCAATTGAAGATCCAAGTGCCCCACATGGACTCCAATTACTCATAAAAGATTA
TCCATATGCTGTTGATGGACTTGACATTTGGGCAGCCATCAAAACATGGGTACGAGAGTA
TTGTTCAATTTACTACAAGAATGATGAAATGATTTGTAATGATCCAGAGCTCAAATCATG
GTGGAATGAAGTTCGAGAAGAGGCCATGAAGACAAGAAAGACGAACCATGGTGGCCAAA
AATGCAAAGTATTGAAGAGCTAATCAATAGTTGCACCATCATCATATGGATTTCTTCGGC
TCTTCATGCTGCAGTTAACTTTGGGCAATATCCTTACGGTGGTTTTCTTCCTAATCGCCC
ATCGACTAGCGTACGATTCTTACCGGAAGAAGGCACATCTGAGTATCTAGAACTGCAGTC
AAATACAGATAAAGCTTTCTTGAAAACATTCACTTCCGAACTACAAGAAAATGATCTTCT
GAATATCACTACAATTCAACTTTTATCCTCACATTCTCTTGATGAGTCCTATTTAGGGCA
AAGAAATGATCCAAACTGGACTTTTGATAAGAATGCTTTAGATGCATTTGAGAATTTCAA
AAGAAAGTTAGTTGAAATTGGGGAAATGATTGGGAAAAGAAACCAAGATCATATGTTGAA
GAATCGAGTTGGACGAGAGGTGAAGATGACATACACTTGCTACTTCCCACTAGTCAACC
TGGCGTTACATGTCGAGGAATTCCCAATAGCATTTCTATTTGA

Figure 1 Continued

SEQ ID No. 2: 9-LOX5_1 allele – protein sequence

\>copy1_prot

MVKGKVTLSRSNWINRPKLKLTLQLISSVKCDPSIGKQGKHGKKIYLQNEGDANNEGERVFSVSFDWDEEIGNPGAI
LVRNNHRFSRFFLKSITLFDLPAFGNIHFDCNSWIHPNRHTHTDHHIFFVNKAYLPHETPEPLQNYREKELEKKRGDG
RRVPKNWENIYDYDVYNDISDLDSNSTNKPPILGGLVPYPRRGRTGRPRSKKDDRYETRCAIKDVYVPSDERFSDLKK
SDFDIHGLRSVLRDIKDKLKASLGKSPKRLESLKDVYAIYEPRSFFRRGKFLMPQVIEGNKSGWRTDEEFAREMLAGV
NPMVIRRLQSFPPTSNLNPSDYGDQNSKITPKQIMNGMEGLTVDQAIAENKLYILDHHDLIPYLKRINTTSTKTYAT
RTLLFLKNDGTLKPLAIELSLPHPQGYQFGAISKILLPDKGRIGEPLWQLAKAYVVVNDSGHHQLSHWLNTHAVIEPF
VIATHRQLSVVHPIHKLLVPHFRYTMKINALARSTLINTDGIIEKTQYPSKYSMEMSSFAYQNWDFTQQALPADLIKR
GIAIEDPSAPHGLQLLIKDYPYAVDGLDIWAAIKTWVREYCSIYYKNDEMICNDPELKSWWNEVRERGHEDKKDEP
WWPKMQSIEELINSCTIIIWISSALHAAVNFGQYPYGGFLPNRPSTSVRFLPEEGTSEYLELQSNTDKAFLKTFTSELQ
ENDLLNITTIQLLSSHSLDESYLGQRNDPNWTFDKNALDAFENFKRKLVEIGEMIGKRNQDHMLKNRVGREVKMTY
TLLLPTSQPGVTCRGIPNSISI-

Figure 2: 9-LOX5_2

SEQ ID No. 3: 9-LOX5_2 allele – coding sequence
>copy2_CDS
ATGGTTAAAGGGAAAGTTACTTTGTCCAGAAGCAATTGGATGAATAGGCCAAAACTAAA
ACTTACCCTACAACTCATCAGCTCTGTCAAGGGTGATCCATCAATAGAAATGCAGGGGAA
ACATGGAAAGAAAATATACTTGCAAAATGAAGGAGATGCAAATAATGAAGGGGAAAGAGT
GTTTAGTGTGAGTTTTGATTGGGATGAAGAGATTGGGAATCCAGGAGCTATCTTGGTAAG
AAACAACCATCGTTTTTCAAGATTCTTCCTCAAATCTATTACTCTTTTTGATGTACCTGC
CTTCGGAAACATCCACTTTGATTGCAACTCTTGGATTCACCCTAATAGACATACACATAC
AGATCATCACATTTTCTTTGTAAATAAGGCATATCTTCCTCATGAGACACCAGAGCCACT
TAAAATGTATAGAGAGAAAGAACTCGAAAAAAGAGAGGAAATGGTAGAAGAGTGCCTAA
AAATTGGGAAAACATATACGACTATGATGTCTACAATGATATTAGTGATTTAGATTCTAA
TTCAACAAATAAACCCCCTATTCTTGGAGGATTAGTGCCTTATCCACGCAGAGGAAGAAC
TGGACGACCATGCTTACAAAATGATGATAGATATGAGACCAGATGTGCAATCAAAGATGT
TTATGTTCCCAGTGATGAAAGATTTAGTGACTTGAAGAAATCAGATTTTGATATTCATGG
ATTAAGATCAGTGCTTCGAGACATTAAAGATAAACTTAAAGCTTCATTAGGAAAATCTCC
TAAAAGATTGGAGTCTCTTAAAGATGTGTATGCAATCTATGAACCACGTTCCTTCTTTCG
ACGAGGGAAATTTCCAATGCCCCAGGTGATCGAAGGTAATAAATCTGGATGGAGGACTGA
TGAAGAGTTCGCTAGAGAAATGTTGGCAGGAGTAAATCCTATGGTCATTCGTCGTCTCCA
AAGTTTCCCACCGACTAGCAACCTTAACCCTAGTGACTATGGTGATCAAAACAGCAAGAT
AACACCAAAACAGATTATGAATGGTATGGAGGGACTTACGGTAGACCAGGCAATTGCAGA
AAACAAGCTGTACATATTAGATCACCATGATTTAATAATTCCATATCTTAAAAGAATAAA
TACAACTTCCACAAAAACTTATGCTACAAGAACACTTCTCTTCCTAAAAAATGATGGGAC
TTTGAAGCCTTTAGCAATTGAATTGAGCTTGCCACACCCTCAAGGATACCAATTTGGAGC
CATTAGTAAAATATTGTTGCCAGATAAAGGAAAAATTGGGGAACCACTTTGGCAACTAGC
TAAAGCTTATGTTGTTGTCAATGACTCTGGTCACCATCAACTCATCAGCCACTGGCTAAA
CACACATGCCGTAATTGAGCCATTTGTGATTGCAACACATAGACAACTCAGTGTTGTTCA
TCCGATTCACAAGTTGCTTGTTCCTCACTTTCGATACACCATGAAGATCAATGCTCTTGC
AAGATCAACCCTCATTAATACTGATGGTATTATTGAGAAAACTCAATATCCTTCTAAGTA
TTCTATGGAGATGTCTTCTTTTGCTTATCAAAATTGGGACCTTACTCAACAAGCACTCCC
TGCTGACCTAATCAAGAGAGGAATTGCAATTGAAGATCCAAGTGCCCCACATGGACTCCA
ATTACTCATAAAAGATTATCCATATGCTGTTGATGGACTTGACATTTGGACAGCCATCAA
AACATGGGTACGAGAGTATTGTTCAATTTACTACAAGAACGATGAAATGATTCGTAATGA
TCCAGAGCTCAAATCATGGTGGAATGAAGTTCGAGAAAGAGGCCATGAAGACAAGAAAGA
CGAACCATGGTGGCCAAAAATGCAAAGTATTGAAGAGCTAATCAATAGTTGCACCATCAT
CATATGGATTTCTTCGGCTCTTCATGCTGCAGTTAACTTTGGGCAATATCCTTACGGTGG
TTTTCTTCCTAATCGCCCATCGACTAGCGTACGATTCTTACCGGAAGAAGGCACATCTGA
GTATCTAGAACTGCAGTCAAATACAGATAAAGCTTTCTTGAAAACATTCACTTCCGAACT
ACAAGAAAATGATCTTCTGAATATCACTACAATTCAACTTTTATCCTCACATTCTCTTGA
TGAGTCCTATTTAGGGCAAAGAAGTGATCCGAACTGGACTTTTGATAAGAATGCTTTAGA
TGCATTTGAGAATTTCAAAAGAAAGTTAGTTGAAATTGGGGAAATGATTGGGAAAGAAA
CAAAGATGATATGTTGAAGAATCGAGCTGGACGAGAGGTGAAGATGACATACACTTTGCT
ACTTCCCACTAGTCAACCTGGCATTACATGTCGAGGAATTCCCAATAGCATTTCTATTTGA

Figure 2 Continued

SEQ ID No. 4: 9-LOX5_2 allele – protein sequence
>copy2_prot
MVKGKVTLSRSNWMNRPKLKLTLQLISSVKGDPSIEMQGKHGKKIYLQNEGDANNEGERVFSVSFDWDEEIGNPG
AILVRNNHRFSRFFLKSITLFDVPAFGNIHFDCNSWIHPNRHTHTDHHIFFVNKAYLPHETPEPLKMYREKELEKKRG
NGRRVPKNWENIYDYDVYNDISDLDSNSTNKPPILGGLVPYPRRGRTGRPCLQNDDRYETRCAIKDVYVPSDERFSD
LKKSDFDIHGLRSVLRDIKDKLKASLGKSPKRLESLKDVYAIYEPRSFFRRGKFPMPQVIEGNKSGWRTDEEFAREML
AGVNPMVIRRLQSFPPTSNLNPSDYGDQNSKJTPKQIMNGMEGLTVDQAIAENKLYILDHHDLIIPYLKRINTTSTKT
YATRTLLFLKNDGTLKPLAIELSLPHPQGYQFGAISKILLPDKGKIGEPLWQLAKAYVVVNDSGHHQLISHWLNTHAV
IEPFVIATHRQLSVVHPIHKLLVPHFRYTMKINALARSTLINTDGIIEKTQYPSKYSMEMSSFAYQNWDLTQQALPAD
LIKRGIAIEDPSAPHGLQLLIKDYPYAVDGLDIWTAIKTWVREYCSIYYKNDEMIRNDPELKSWWNEVRERGHEDKK
DEPWWPKMQSIEELINSCTIIIWISSALHAAVNFGQYPYGGFLPNRPSTSVRFLPEEGTSEYLELQSNTDKAFLKTFTS
ELQENDLLNITTIQLLSSHSLDESYLGQRSDPNWTFDKNALDAFENFKRKLVEIGEMIGKRNKDDMLKNRAGREVK
MTYTLLLPTSQPGITCRGIPNSISI-

Figure 3: 9-LOX5_3

SEQ ID No. 5: 9-LOX5_3 allele – coding sequence
>recomb4513-5_CDS

```
ATGGTTAAAGGGAAAGTTACTTTGTCCAGAAGCAATTGGATCAATAGGCCAAAACTAAA
ACTTACCCTACAACTCATCAGCTCTGTGAAGTGTGATCCATCAATAGAAATGCAGGGGAA
ACATGGAAAGAAAATATACTTGCAAAATGAAGGAGATGCAAATAATGAAGGGGAAAGAGT
GTTTAGTGTGAGTTTTGATTGGGATGAAGAGATTGGGAATCCAGGAGCTATCTTGGTAAG
AAACAACCATCGTTTTTCAAGATTCTTCCTCAAATCTATTACTCTTTTTGATGTACCTGC
CTTCGGAAACATCCACTTTGATTGCAACTCTTGGATTCACCCTAATAGACATACACATAC
AGATCATCACATTTTCTTTGTAAATAAGGCATATCTTCCTCATGAGACACCAGAGCCACT
TAAAATGTATAGAGAGAAAGAACTCGAAAAAAGAGAGGAAATGGTAGAAGAGTGCCTAA
AAATTGGGAAAACATATACGACTATGATGTCTACAATGATATTAGTGATTTAGATTCTAA
TTCAACAAATAAACCCCCTATTCTTGGAGGATTAGTGCCTTATCCACGCAGAGGAAGAAC
TGGACGACCATGCTTACAAAATGATGATAGATATGAGACCAGATGTGCAATCAAAGATGT
TTATGTTCCCAGTGATGAAAGATTTAGTGACTTGAAGAAATCAGATTTTGATATTCATGG
ATTAAGATCAGTGCTTCGAGACATTAAAGATAAACTTAAAGCTTCATTAGGAAAATCTCC
TAAAAGATTGGAGTCTCTTAAAGATGTGTATGCAATCTATGAACCACGTTCCTTCTTTCG
ACGAGGGAAATTTCCAATGCCCCAGGTGATCGAAGGTAATAAATCTGGATGGAGGACTGA
TGAAGAGTTCGCTAGAGAAATGTTGGCAGGAGTAAATCCTATGGTCATTCGTCGTCTCCA
AAGTTTCCCACCGACTAGCAACCTTAACCCTAGTGACTATGGTGATCAAAACAGCAAGAT
AACACCAAAACAGATTATGAATGGTATGGAGGGACTTACGGTAGACCAGGCAATTGCAGA
AAACAAGCTGTACATATTAGATCACCATGATTTAATAATTCCATATCTTAAAAGAATAAA
TACAACTTCCACAAAAACTTATGCTACAAGAACACTTCTCTTCCTAAAAAATGATGGGAC
TTTGAAGCCTTTAGCAATTGAATTGAGCTTGCCACACCCTCAAGGATACCAATTTGGAGC
CATTAGTAAAATATTGTTGCCAGATAAAGGAAAAATTGGGGAACCACTTTGGCAACTAGC
TAAAGCTTATGTTGTTGTCAATGACTCTGGTCACCATCAACTCATCAGCCACTGGCTAAA
CACACATGCCGTAATTGAGCCATTTGTGATTGCAACACATAGACAACTCAGTGTTGTTCA
TCCGATTCACAAGTTGCTTGTTCCTCACTTTCGATACACCATGAAGATCAATGCTCTTGC
AAGATCAACCCTCATTAATACTGATGGTATTATTGAGAAACTCAATATCCTTCTAAGTA
TTCTATGGAGATGTCTTCTTTTGCTTATCAAAATTGGGACCTTACTCAACAAGCACTCCC
TGCTGACCTAATCAAGAGAGGAATTGCAATTGAAGATCCAAGTGCCCCACATGGACTCCA
ATTACTCATAAAAGATTATCCATATGCTGTTGATGGACTTGACATTTGGACAGCCATCAA
AACATGGGTACGAGAGTATTGTTCAATTTACTACAAGAACGATGAAATGATTCGTAATGA
TCCAGAGCTCAAATCATGGTGGAATGAAGTTCGAGAAAGAGGCCATGAAGACAAGAAAGA
CGAACCATGGTGGCCAAAAATGCAAAGTATTGAAGAGCTAATCAATAGTTGCACCATCAT
CATATGGATTTCTTCGGCTCTTCATGCTGCAGTTAACTTTGGGCAATATCCTTACGGTGG
TTTTCTTCCTAATCGCCCATCGACTAGCGTACGATTCTTACCGGAAGAAGGCACATCTGA
GTATCTAGAACTGCAGTCAAATACAGATAAAGCTTTCTTGAAAACATTCACTTCCGAACT
ACAAGAAATGATCTTCTGAATATCACTACAATTCAACTTTTATCCTCACATTCTCTTGA
TGAGTCCTATTTAGGGCAAAGAAGTGATCCGAACTGGACTTTTGATAAGAATGCTTTAGA
TGCATTTGAGAATTTCAAAAGAAAGTTAGTTGAAATTGGGGAAATGATTGGGAAAGAAA
CAAAGATGATATGTTGAAGAATCGAGCTGGACGAGAGGTGAAGATGACATACACTTTGCT
ACTTCCCACTAGTCAACCTGGCATTACATGTCGAGGAATTCCCAATAGCATTTCTATTTGA
```

Figure 3 Continued

SEQ ID No. 6: 9-LOX5_3 allele – protein sequence
>recomb4513-5_prot
MVKGKVTLSRSNWINRPKLKLTLQLISSVKCDPSIEMQGKHGKKIYLQNEGDANNEGERVFSVSFDWDEEIGNPGA
ILVRNNHRFSRFFLKSITLFDVPAFGNIHFDCNSWIHPNRHTHTDHHIFFVNKAYLPHETPEPLKMYREKELEKKRGN
GRRVPKNWENIYDYDVYNDISDLDSNSTNKPPILGGLVPYPRRGRTGRPCLQNDDRYETRCAIKDVYVPSDERFSDL
KKSDFDIHGLRSVLRDIKDKLKASLGKSPKRLESLKDVYAIYEPRSFFRRGKFPMPQVIEGNKSGWRTDEEFAREMLA
GVNPMVIRRLQSFPPTSNLNPSDYGDQNSKITPKQIMNGMEGLTVDQAIAENKLYILDHHDLIPYLKRINTTSTKTY
ATRTLLFLKNDGTLKPLAIELSLPHPQGYQFGAISKILLPDKGKIGEPLWQLAKAYVVVNDSGHHQLISHWLNTHAVI
EPFVIATHRQLSVVHPIHKLLVPHFRYTMKINALARSTLINTDGIIEKTQYPSKYSMEMSSFAYQNWDLTQQALPADL
IKRGIAIEDPSAPHGLQLLIKDYPYAVDGLDIWTAIKTWVREYCSIYYKNDEMIRNDPELKSWWNEVRERGHEDKKD
EPWWPKMQSIEELINSCTIIWISSALHAAVNFGQYPYGGFLPNRPSTSVRFLPEEGTSEYLELQSNTDKAFLKTFTSEL
QENDLLNITTIQLLSSHSLDESYLGQRSDPNWTFDKNALDAFENFKRKLVEIGEMIGKRNKDDMLKNRAGREVKMT
YTLLLPTSQPGITCRGIPNSISIns# 9-LOX5 GENE VARIANT PROVIDING POWDERY MILDEW RESISTANCE

RELATED APPLICATIONS AND INCORPORATION BY REFERENCE

This application is a continuation-in-part application of international patent application Serial No. PCT/EP2020/085930 filed 14 Dec. 2020, which published as PCT Publication No. WO 2021/116486 on 17 Jun. 2021, which claims benefit of international patent application Serial No. PCT/EP2019/085169 filed 13 Dec. 2019.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy was created Dec. 14, 2020, is named Y7954-00521SL.txt and is 58,172 bytes in size.

FIELD OF THE INVENTION

The present invention relates to a gene variant that provides powdery mildew resistance to a plant. The invention further relates to a method for producing such a plant, and a method for the identification of the presence of the gene variant in such a plant. The invention further relates to a powdery mildew resistant plant or seed with the gene variant.

BACKGROUND OF THE INVENTION

Powdery mildew is a fungal disease that affects a broad range of plant species in both open and protected cultivation. The fungi causing powdery mildews belong to the family of Erysiphaceae. Two common members that have a large host range and are found throughout the world are *Podosphaera xanthii* and *Golovinomyces cichoracearum*. Symptoms of powdery mildew usually start with small, white, powdery spots on upper leaf surfaces. As the disease progresses, the spots grow larger and denser and cover more parts of the plant. Severe infection can result in early leaf senescence, which directly or indirectly leads to a reduction in yield since this will also affect fruit development and quality.

Even though a number of powdery mildew resistance genes has been identified, in several crops there is still a lack of cultivars that are resistant to this disease. The main powdery mildew control in many regions therefore remains the repeated application of fungicides to minimize the impact of the disease. There is thus a need for the provision of genes that lead to powdery mildew resistance.

Citation or identification of any document in this application is not an admission that such document is available as prior art to the present invention.

SUMMARY OF THE INVENTION

It is therefore an object of the present invention to provide a gene conferring powdery mildew resistance.

The present invention provides a variant of a 9-LOX5 gene that provides powdery mildew resistance to a plant.

The present invention involves a plant which may comprise a copy number variation (CNV) of a 9-LOX5 gene, which CNV comprises at least 2 copies of a 9-LOX5 gene on the same chromosome, wherein the 9-LOX5 gene may comprise SEQ ID NO: 1, or a sequence having at least 60% sequence identity to SEQ ID NO: 1, and wherein the presence of the CNV leads to powdery mildew resistance in the plant.

The invention further relates to 9-LOX5 nucleic acid molecules, methods for selecting powdery mildew resistant plants, the plants obtained and seeds and parts thereof.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seed of *Citrullus lanatus* 19R.901 was deposited with NCIMB Ltd, Ferguson Building, Craibstone Estate, Bucksburn, Aberdeen AB21 9YA, UK on 6 Mar. 2019 under deposit accession number NCIMB 43368.

Seed of *Citrullus lanatus* 19R.909 was deposited with NCIMB Ltd, Ferguson Building, Craibstone Estate, Bucksburn, Aberdeen AB21 9YA, UK on 31 Oct. 2019 under deposit accession number NCIMB 43508.

The Deposits with NCIMB Ltd, under deposit accession numbers NCIMB 43368 and NCIMB 43508 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1—coding sequence (CDS) of the 9-LOX5_1 allele (SEQ ID NO: 1) and the encoded protein (SEQ ID NO: 2).

FIG. 2—coding sequence (CDS) of the 9-LOX5_2 allele (SEQ ID NO: 3) and the encoded protein (SEQ ID NO: 4).

FIG. 3—Coding sequence (SEQ ID NO: 5) and protein sequence (SEQ ID NO: 6) of the 9-LOX5 recombinant that reduced the presence of two different alleles in a resistant line to the presence of only one recombinant allele. The recombinant having only one recombinant 9-LOX5_3 allele is susceptible to powdery mildew.

FIG. 5—9-LOX5 alleles in resistant and susceptible lines. The reads of NCIMB 43368 show the presence of one 9-LOX5_1 allele and one 9-LOX52 allele on the same chromosome. The reads of NCIMB 43508 show that it has two 9-LOX5_2 alleles on the same chromosome. The RZ3378_1 reads show that it has two 9-LOX5_1 alleles on the same chromosome. RZ-W and RZ-900 have only one 9-LOX5_2 allele.

FIG. 6—length of the CNV region and readdepths in different resistant genotypes, as compared to the susceptible RZ-900. See also Table 1. The shadowed bar show the length of the CNV region in each line. RZ-900 has no CNV. The number behind the indication of the line shows the estimated readdepth of the CNV region in that line, which is an indication of the number of copies that is present.

DETAILED DESCRIPTION OF THE INVENTION

Figure 4:
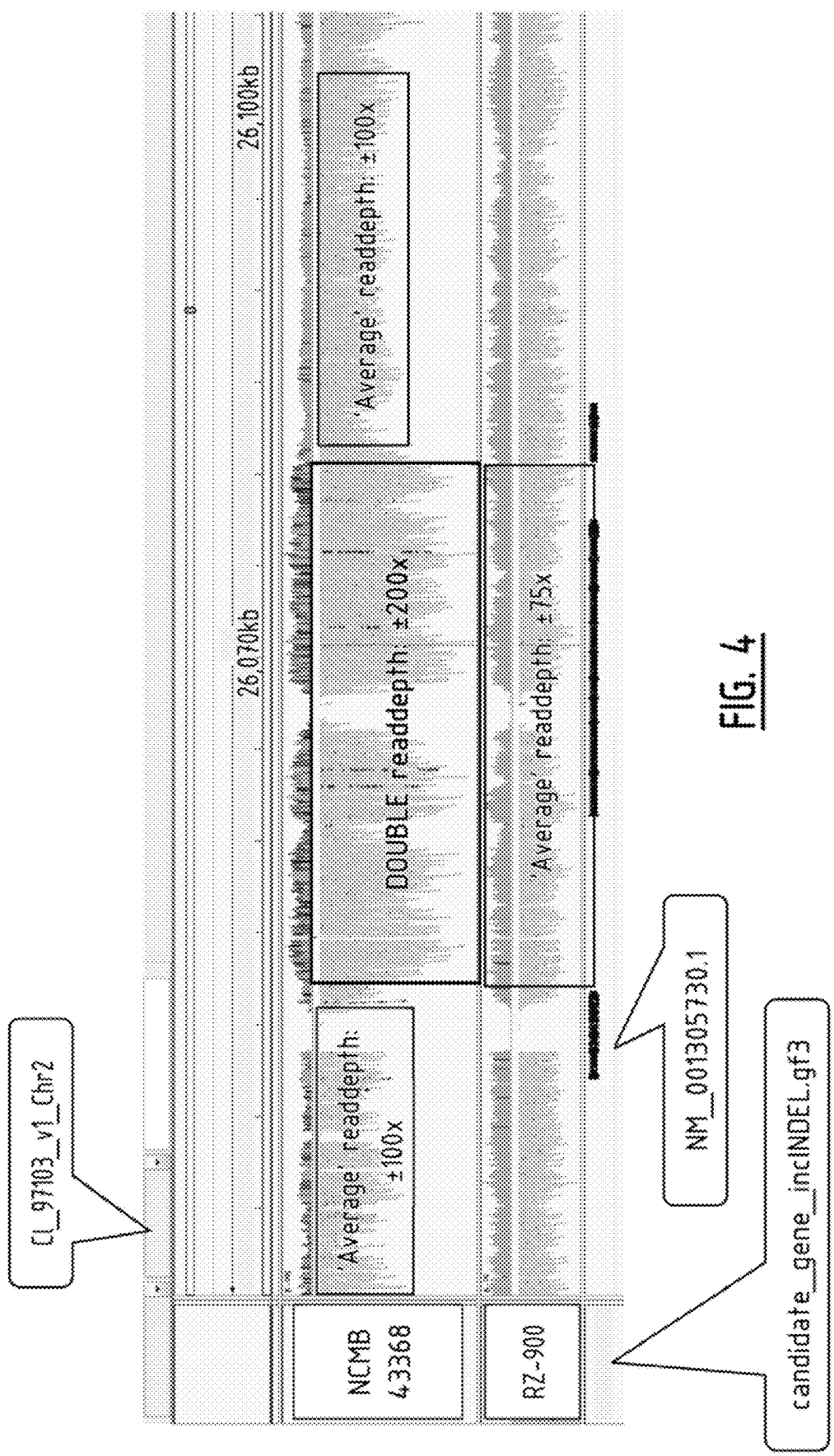
FIG. 4—Read depth analysis of sequencing data from the NCIMB 43368 resistant genotype and the RZ-900 susceptible genotype. The region with the double readdepth indicates the presence of the CNV.

Lipoxygenases (LOXs) are a large family of non-heme iron-containing enzymes that are found in both plants and animals. In plants their activity is widespread; LOXs are found to be involved in a large number of diverse processes in all plant development stages, which include seed storage, germination, fruit ripening, signaling of and reaction on pathogen attack, and signaling of and defense to wounding.

The most common substrates for LOXs in plants are linolenic and linoleic acids. The majority of plant LOXs can be categorized into 9-lipoxygenases (9-LOXs) and 13-lipoxygenases (13-LOXs) depending on whether they catalyze dioxygenation of these substrates at either position 13 or position 9 of their carbon chains. The hydroperoxide products of this LOX reaction are further converted through various pathways that result in compounds having a broad range of functions in plant growth and development. Among these are jasmonic acid, methyl jasmonate, various green leaf volatiles, and death acids.

LOXgenes can also be classified into two subfamilies based on their primary structure and overall sequence similarity. Type-1 LOXs harbor no plastidic transit peptides and have a high sequence similarity (>75%) to one another; both 9-LOXs and 13-LOXs are found in this class. Type-2 LOXs are those that carry a plastidic transit peptide sequence; they show only a moderate sequence similarity (~35%) to one another. So far only 13-LOXs are categorized into this type.

Plants can harbor a large number of LOX genes; the typical conserved motif that is present in mostLOXgenes is a 38-amino acid residue represented by $His-(X)_4-His-(X)_4-His-(X)_{17}-His-(X)_8-His$. The genome of Arabidopsis thaliana comprises 6 genes predicted to be LOXs, the Zea mays genome contains a total of 13 genes predicted to be LOX genes, whereas in Capsicum annuum 8 LOX genes have been identified. In some members of the Cucurbitaceae family the number is much higher, with 23 predicted LOXs in Cucumis sativus and 26 in Citrullus lanatus. In C. sativus, 19 of the 23 LOXs are present in tandem clusters on chromosome 2, chromosome 4, and on an unmapped scaffold. In C. lanatus 19 of the 26 LOXs are arranged in two tandem gene arrays on chromosome 2.

The region on chromosome 2 of Citrullus lanatus that comprises a number of LOX genes was found to be involved in powdery mildew resistance through QTL mapping and subsequent fine-mapping. Internal research on powdery mildew resistant sources for Citrullus lanatus determined that the presence of multiple copies of a 9-LOX5 gene on the same chromosome, i.e. the presence of a copy number variation (CNV) for 9-LOX5, leads to resistance to powdery mildew. Transfer of the CNV of the 9-LOX5 gene from a powdery mildew resistant plant to a powdery mildew susceptible plant provided resistance to the susceptible plant. As used herein, multiple copies comprise 2 copies, 3 copies, 4 copies, or more than 4 copies.

The presence of a copy number variation of a gene, such as the 9-LOX5 gene of the invention, can be determined through techniques that are known to the skilled person. An example of the identification of a CNV region, in particular the CNV region of the present invention, is described in Example 1.

It was particularly surprising that a 9-LOX5 gene was the cause of powdery mildew resistance, since an earlier study on the involvement of LOXgenes in powdery mildew resistance in cucumber had shown that other LOX genes than LOX5 were expected to be involved in the resistance. The CsLOX5 gene did not show a change in expression profile after powdery mildew infection and was therefore determined to be a less likely candidate (Oh et al, Expression of cucumber LOX genes in response to powdery mildew and defense-related signal molecules. Can. J. Plant Sci. 94:845-850, 2014).

Further internal research determined that quite some allelic variation exists within the 9-LOX5 gene. One allele of the 9-LOX5 gene of the present invention in Citrullus lanatus, designated 9-LOX5_1, may comprise SEQ ID NO: 1 (CDS), and the encoded protein may comprise SEQ ID NO: 2. Another version, i.e. another allele, of the same 9-LOX5 gene of the present invention in Citrullus lanatus, designated 9-LOX5_2, may comprise SEQ ID NO: 3 (CDS), and the encoded protein may comprise SEQ ID NO: 4. The sequence identity between these two alleles is 99% on CDS level and 97% on protein level.

An allele is a variant form of a certain gene, which for the present invention is a form of the 9-LOX5 gene as defined herein. In the context of the present application a gene also may comprise a nucleic acid molecule having the sequence or similar sequence of said gene, and an allele also may comprise a nucleic acid molecule having the sequence or similar sequence of the variant form of said gene.

Figure 5:
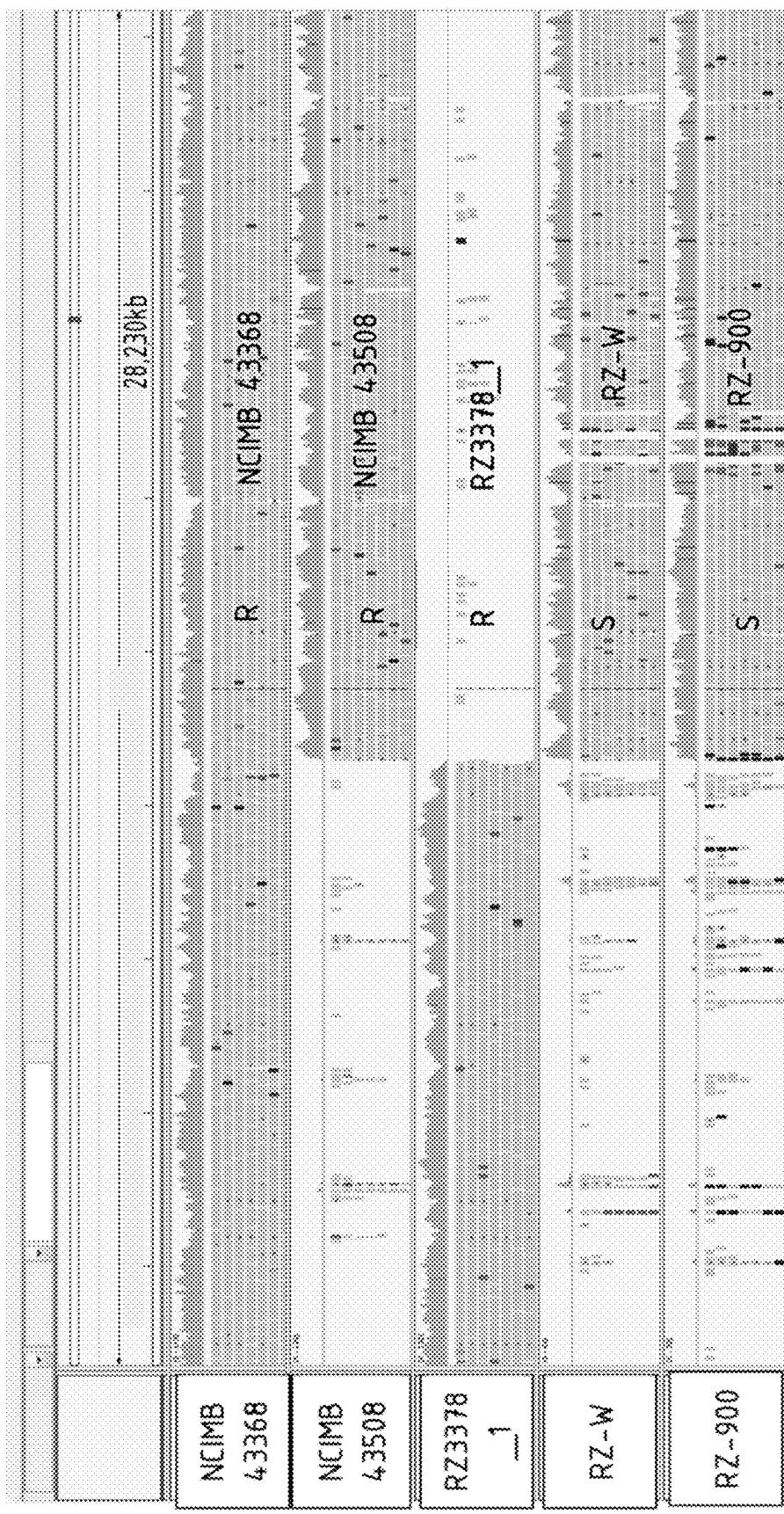

The 9-LOX5 copies within the CNV can be present in different combinations on the same chromosome, e.g. multiple copies of an allele which may comprise SEQ ID NO: 1, multiple copies of an allele which may comprise SEQ ID NO: 3, or one or more alleles which may comprise SEQ ID NO: 1 and one or more alleles which may comprise SEQ ID NO: 3, would all lead to resistance to powdery mildew (Example 2, FIG. 5).

Although often allelic variation is the cause of a certain phenotype such as resistance, in this instance it was surprisingly found that the presence of a specific allele could not be linked to resistance. For example, a plant having only one copy of the 9-LOX5_1 allele was susceptible to powdery mildew, and a plant having only one copy of the 9-LOX5_2 was susceptible as well. In addition, other variations between those alleles were observed which on itself could not be linked to resistance. Powdery mildew resistance is therefore only caused by the presence of a CNV which may comprise multiple copies of any 9-LOX5 allele combination on the same chromosome.

The present invention provides a plant which may comprise a copy number variation (CNV) of a 9-LOX5 gene, which CNV may comprise at least 2 copies on the same chromosome of a 9-LOX5 gene which may comprise SEQ ID NO: 1, or a sequence having at least 60% sequence identity to SEQ ID NO: 1, wherein the presence of the CNV leads to powdery mildew resistance in the plant.

The present invention provides a plant which may comprise a copy number variation (CNV) of multiple 9-LOX5 alleles on the same chromosome which may comprise SEQ ID NO: 1, or a plant which may comprise a CNV of multiple 9-LOX5 alleles on the same chromosome which may comprise SEQ ID NO: 3, or a plant which may comprise a CNV of multiple 9-LOX5 alleles on the same chromosome which may comprise SEQ ID NO: 1 and SEQ ID NO: 3, wherein the CNV provides powdery mildew resistance.

The present invention in particular relates to the following embodiments: a plant which may comprise a CNV which may comprise two copies of SEQ ID NO: 1 or of a similar sequence; or which may comprise three copies of SEQ ID NO: 1 or of a similar sequence; or which may comprise four copies of SEQ ID NO: 1 or of a similar sequence; or which may comprise five copies of SEQ ID NO: 1 or of a similar sequence; or which may comprise two copies of SEQ ID NO: 3 or of a similar sequence; or which may comprise three copies of SEQ ID NO: 3 or of a similar sequence; or which may comprise four copies of SEQ ID NO: 3 or of a similar sequence; or which may comprise five copies of SEQ ID NO: 3 or of a similar sequence; or which may comprise one copy of SEQ ID NO: 1 or of a similar sequence and one copy of SEQ ID NO: 3 or of a similar sequence; or which may comprise two copies of SEQ ID NO: 1 or of a similar sequence and one copy of SEQ ID NO: 3 or of a similar sequence; or which may comprise three copies of SEQ ID NO: 1 or of a similar sequence and one copy of SEQ ID NO: 3 or of a similar sequence; or which may comprise four copies of SEQ ID NO: 1 or of a similar sequence and one copy of SEQ ID NO: 3 or of a similar sequence; or which may comprise two copies of SEQ ID NO: 1 or of a similar sequence and two copies of SEQ ID NO: 3 or of a similar sequence; or which may comprise two copies of SEQ ID NO: 1 or of a similar sequence and three copies of SEQ ID NO: 3 or of a similar sequence; or which may comprise three copies of SEQ ID NO: 1 or of a similar sequence and two copies of SEQ ID NO: 3 or of a similar sequence. In a preferred embodiment the present invention relates to a plant which may comprise a CNV that may comprise one copy of SEQ ID NO: 1 and one copy of SEQ ID NO: 3.

As used herein, a CNV is a copy number variation which may comprise two or more alleles of the same gene on one chromosome. For the present invention, the presence of a CNV means that two or more alleles of the 9-LOX5 gene as defined herein are present on the same chromosome. The alleles can be the same or different but are both representatives of the same gene. Alleles belonging to the 9-LOX5 gene of the invention have, in order of increased preference, a sequence identity of at least 60%, 65%, 70%, 75%, 80%, 85%, 87%, 90%, 91%, 92%, 93%, 94%, 95%, 96%, 97%, 98%, 99%, or 100% to SEQ ID NO: 1.

An allele that is similar to the 9-LOX51 allele has a sequence identity of at least 60%, 65%, 70%, 75%, 80%, 85%, 87%, 90%, 91%, 92%, 93%, 94%, 95%, 96%, 97%, 98%, or 99% to SEQ ID NO: 1. An allele that is similar to the 9-LOX5_2 allele has a sequence identity of at least 60%, 65%, 70%, 75%, 80%, 85%, 87%, 90%, 91%, 92%, 93%, 94%, 95%, 96%, 97%, 98%, or 99% to SEQ ID NO: 3. An allele of the 9-LOX5 gene can be similar to both the 9-LOX51 and 9-LOX52 alleles since there can be overlap between the sequence identity percentages.

An allele comprising SEQ ID NO: 1 encodes a protein comprising SEQ ID NO: 2. An allele comprising SEQ ID NO: 3 encodes a protein comprising SEQ ID NO: 4. An allele of the 9-LOX5 gene of the present invention encodes a protein having a sequence identity of, in order of increased preference, at least 60%, 65%, 70%, 75%, 80%, 85%, 87%, 90%, 91%, 92%, 93%, 94%, 95%, 96%, 97%, 98%, 99%, or 100% to SEQ ID NO: 2.

An allele that is similar to the 9-LOX51 allele encodes a protein that has a sequence identity of at least 60%, 65%, 70%, 75%, 80%, 85%, 87%, 90%, 91%, 92%, 93%, 94%, 95%, 96%, 97%, 98%, or 99% to SEQ ID NO: 2. An allele that is similar to the 9-LOX5_2 allele encodes a protein that has a sequence identity of at least 60%, 65%, 70%, 75%, 80%, 85%, 87%, 90%, 91%, 92%, 93%, 94%, 95%, 96%, 97%, 98%, or 99% to SEQ ID NO: 4.

As used herein, sequence identity is the percentage of nucleotides or amino acids that is identical between two sequences after proper alignment of those sequences. The person skilled in the art is aware of how to align sequences, for example by using a sequence alignment tool such as BLAST®, which can be used for both nucleotide sequences and protein sequences. To obtain the most significant result, the best possible alignment that gives the highest sequence identity score should be obtained. The sequences are compared over the length of the shortest sequence in the assessment.

A high percentage of sequence identity is commonly assumed to point to a homologous sequence. An allele of a 9-LOX5 gene having a sequence identity percentage as claimed is part of the invention if said similar sequence is functionally homologous. Functionally homologous means that it is a gene sequence that leads to a protein that has the same function as the 9-LOX5 protein that was identified in Citrullus lanatus, wherein the same function is that it provides resistance to powdery mildew. A similar sequence of the 9-LOX5 gene is a sequence that has at least 60%, 65%, 70%, 75%, 80%, 85%, 87%, 90%, 91%, 92%, 93%, 94%, 95%, 96%, 97%, 98%, or 99% sequence identity to SEQ ID NO: 1. For the present invention, 'functionally homologous' means that the gene or protein provides powdery mildew resistance.

The present invention relates to a nucleic acid molecule which may comprise two or more alleles of the 9-LOX5 gene. The present invention relates to the following embodiments: a nucleic acid molecule which may comprise two copies of SEQ ID NO: 1 or of a similar sequence; three copies of SEQ ID NO: 1 or of a similar sequence; four copies of SEQ ID NO: 1 or of a similar sequence; five copies of SEQ ID NO: 1 or of a similar sequence; two copies of SEQ ID NO: 3 or of a similar sequence; three copies of SEQ ID NO: 3 or of a similar sequence; four copies of SEQ ID NO: 3 or of a similar sequence; five copies of SEQ ID NO: 3 or of a similar sequence; one copy of SEQ ID NO: 1 or of a similar sequence and one copy of SEQ ID NO: 3 or of a similar sequence; two copies of SEQ ID NO: 1 or of a similar sequence and one copy of SEQ ID NO: 3 or of a similar sequence; three copies of SEQ ID NO: 1 or of a similar sequence and one copy of SEQ ID NO: 3 or of a similar sequence; four copies of SEQ ID NO: 1 or of a similar sequence and one copy of SEQ ID NO: 3 or of a similar sequence; two copies of SEQ ID NO: 1 or of a similar sequence and two copies of SEQ ID NO: 3 or of a similar sequence; two copies of SEQ ID NO: 1 or of a similar sequence and three copies of SEQ ID NO: 3 or of a similar sequence; three copies of SEQ ID NO: 1 or of a similar sequence and two copies of SEQ ID NO: 3 or of a similar sequence. In a preferred embodiment the present invention relates to a nucleic acid molecule that may comprise one copy of SEQ ID NO: 1 or of a similar sequence and one copy of SEQ ID NO: 3 or of a similar sequence.

As used herein, resistance to powdery mildew is resistance to at least *Podosphaera xanthii* ((Castagne) U. Braun & Shishkoff), and optionally also resistance to *Golovinomyces cichoracearum* ((DC.) V. P. Heluta). Resistance to *Podosphaera xanthii* is in particular resistance to race 1 W and 2 W.

The presence of the resistance of the invention can be determined by performing a bio-assay using a leaf-disc assay. This assay can be performed by taking leaf-discs of around 1.5 cm in diameter from plants that are at 2-true leaf stage. These leaf-discs are put in a box that can for example hold 32 discs. At least one leaf-disc of a susceptible control should be included, to check if the bio-assay is properly performed. If available, also at least one resistant control should be included. For the susceptible control in such a bio-assay a plant of variety Sugarlee can be used, or a plant of variety RZ-900, or a plant of PI296341. Sugarlee and RZ-900 have one copy of the 9-LOX5_2 allele comprising SEQ ID NO: 3. PI296341 has one copy of the 9-LOX5_1 allele comprising SEQ ID NO: 1. This confirms that a plant having only one copy of a 9-LOX5 allele is susceptible to powdery mildew resistance. As a resistant control a plant deposited as NCIIB 43368 or a plant deposited as NCIMB 43508 can be used. A plant of NCIIB 43368 homozygously may comprise a CNV of the 9-LOX5 gene of the invention which may comprise one copy of the 9-LOX5_1 allele which may comprise SEQ ID NO: 1 and one copy of the 9-LOX5_2 allele which may comprise SEQ ID NO: 3. A plant of NCIMB 43508 homozygously may comprise a CNV of the 9-LOX5 gene of the invention which may comprise two copies of the 9-LOX5_2 allele which may comprise SEQ ID NO: 3.

One day after taking the leaf-discs they are inoculated by blowing air from infected watermelon seedlings onto the discs to be tested. To get the infected watermelon seedlings, plants are grown at 25° C./18° C. day/night temperature. At cotyledon stage they are infected by brushing powdery mildew spores onto the cotyledons. After that they are kept for 10-12 days in a phytotron chamber at 22° C. day and 20° C. night temperature, under 12/12 hours light/dark conditions. After 10-12 days the inoculum is ready to be used in the bio-assay.

After inoculation the boxes with the leaf-discs are also kept in a phytotron chamber at 22° C. day and 20° C. night temperature, under 12/12 hours light/dark conditions. After 10-12 days scoring can be done; the susceptible controls should then have a score of 4.0 or higher than 4.0 according to the symptom description of Table 2.

As used herein, a plant or line is resistant when the average score of the bio-assay is 3.0 or lower than 3.0 according to the symptom description of Table 2. A plant of the invention has preferably a score of 2.5 or lower than 2.5, most preferably a score of 2.0 or lower than 2.0.

A plant of the invention is preferably a cultivated plant which is non-wild and has agronomical value, and is in particular agronomically elite. A plant of the invention is preferably a plant of the Cucurbitaceae family, which may comprise a plant of the species *Citrullus lanatus, Cucumis melo, Cucumis sativus, Cucurbita pepo, Cucurbita maxima,* or *Cucurbita moschata*. In a preferred embodiment a plant of the invention is a plant of the species *Citrullus lanatus*. A *Citrullus lanatus* plant of the present invention is a plant that produces fruits having red flesh or yellow flesh, and a *Citrullus lanatus* plant of the present invention is in particular not a plant that produces fruits having white flesh.

A plant of the invention may comprise the CNV of the 9-LOX5 gene homozygously or heterozygously. When the CNV is homozygously present, both chromosomes on which the 9-LOX5 gene resides in the plant comprise a 9-LOX5 CNV. When the CNV is heterozygously present, only one of the chromosomes on which the 9-LOX5 gene resides in the plant may comprise a 9-LOX5 CNV.

The present invention relates to a nucleotide sequence which may comprise a copy number variation (CNV) of the 9-LOX5 gene of the invention. The nucleotide sequence may comprise two or more 9-LOX5_1 alleles which may comprise SEQ ID NO: 1 on the same chromosome, or two or more 9-LOX5_2 alleles which may comprise SEQ ID NO: 3 on the same chromosome, or a combination of at least one 9-LOX5_1 allele which may comprise SEQ ID NO: 1 and at least one 9-LOX52 allele which may comprise SEQ ID NO: 3 on the same chromosome.

A plant of the invention may comprise a plant of an inbred line, a hybrid, an open pollinated variety, a doubled haploid, or a plant of a segregating population.

The invention further relates to a seed that may comprise the CNV of the 9-LOX5 gene of the invention, which seed can grow into a plant of the invention. The invention also relates to a plant part of a plant of the invention, which may comprise a fruit of a plant of the invention, optionally in processed form.

The present invention relates to a method for producing a plant that is resistant to powdery mildew, which may comprise introducing a copy number variation (CNV) of a 9-LOX5 gene which may comprise one or more copies of a 9-LOX5_1 allele having SEQ ID NO: 1 and/or one or more copies of a 9-LOX5_2 allele having SEQ ID NO: 3 into a plant. Said method may comprise the introduction of a nucleotide sequence which may comprise two or more 9-LOX5_1 alleles which may comprise SEQ ID NO: 1 on the same chromosome, or two or more 9-LOX5_2 alleles which may comprise SEQ ID NO: 3 on the same chromosome, or a combination of at least one 9-LOX5_1 allele which may comprise SEQ ID NO: 1 and at least one 9-LOX5_2 allele which may comprise SEQ ID NO: 3 on the same chromosome. Introduction of this CNV sequence can be done through introgression from a plant which may comprise said nucleotide sequences, for example from a plant that was deposited as NCIIB 43368 or from a plant that was deposited as NCIMB 43508. The CNV sequence can also be introduced from a plant from a related *Citrullus* species that is resistant to powdery mildew caused by a 9-LOX5 CNV, for example a plant of the species *Citrullus mucusospermus* or a plant of the species *Citrullus amarus*. These species are not agronomically elite and do not form a part of the present invention, but in research related to the present invention certain resistant plants of these species were found to have the 9-LOX5 CNV of this invention, and the CNV was also determined to be the cause of the resistance. Resistant plants of these species that comprise the 9-LOX5 CNV of this invention can therefore be used as sources for producing a *Citrullus lanatus* plant that is resistant to powdery mildew. Breeding methods such as crossing and selection, backcrossing, recombinant selection, or other breeding methods that result in the transfer of a genetic sequence from a resistant plant to a susceptible plant can be used. A plant produced by such method is also a part of the invention.

Transgenic techniques used for transferring sequences between plants that are sexually incompatible can also be used to produce a plant of the invention, by transferring the CNV of the 9-LOX5 gene. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention. Genome editing can be used to develop a powdery mildew resistant plant through duplication of the region which may comprise an allele of the 9-LOX5 gene of the invention. Cis-genetic techniques that make the transfer of sequences between plants that can be crossed with each other, optionally of a crossable but different species, more efficient can also be used to produce a plant of the invention.

The present invention relates to a method for selecting a powdery mildew resistant plant, wherein the selection may comprise determining the presence of a CNV of the 9-LOX5 gene of the invention in the genome of the plant. Determining the presence of said CNV may comprise identification of the presence of multiple copies of the 9-LOX5 gene, which copies can be one or more 9-LOX5_1 alleles which may comprise SEQ ID NO: 1 and/or one or more 9-LOX5_2 alleles which may comprise SEQ ID NO: 3. A plant in which the CNV of the 9-LOX5 gene is identified is subsequently selected as a powdery mildew resistant plant. Optionally the powdery mildew resistance can be confirmed by performing a bio-assay as described in Example 4. The selected plant obtained by such method is also a part of this invention.

The presence of a CNV of the 9-LOX5 gene can be determined through a readdepth analysis, as is described in Example 1. In certain situations another way to identify the presence of a CNV of the 9-LOX5 gene is through the use of molecular markers.

The invention also relates to a method for the production of a powdery mildew resistant plant, said method which may comprise:

a) crossing a plant which may comprise a CNV of the 9-LOX5 gene of the invention with a plant not which may comprise said CNV;
b) optionally performing one or more rounds of selfing and/or crossing a plant resulting from step a) to obtain a further generation population;
c) selecting from the population a plant that may comprise the CNV of the 9-LOX5 gene that is resistant to powdery mildew.

The invention also relates to a method for the production of a powdery mildew resistant plant, said method which may comprise:

a) crossing a plant which may comprise a CNV of the 9-LOX5 gene of the invention with a plant not which may comprise said CNV;
b) backcrossing the plant resulting from step a) with the parent not which may comprise the CNV for at least three generations;
c) selecting from the third or higher backcross population a plant that may comprise the CNV of the 9-LOX5 gene that is resistant to powdery mildew.

The invention also relates to propagation material suitable for producing a plant of the invention, wherein the propagation material is suitable for sexual reproduction, and is in particular selected from a microspore, pollen, an ovary, an ovule, an embryo sac, or an egg cell, or is suitable for vegetative reproduction, and is in particular selected from a cutting, a root, a stem cell, or a protoplast, or is suitable for tissue culture of regenerable cells, and is in particular selected from a leaf, pollen, an embryo, a cotyledon, a hypocotyl, a meristematic cell, a root, a root tip, an anther, a flower, a seed and a stem, and wherein the plant produced from the propagation material may comprise the CNV of the 9-LOX5 gene of the invention that provides powdery mildew resistance. A plant of the invention may be used as a source of the propagation material. A tissue culture which may comprise regenerable cells also forms a part of this invention.

The invention further relates to a cell of a plant of the invention. Such a cell may either be in isolated form or a part of the complete plant or parts thereof and still forms a cell of the invention because such a cell may comprise the CNV of the 9-LOX5 gene of the invention. Each cell of a plant of the invention carries the CNV of the 9-LOX5 gene of the invention. A cell of the invention may also be a regenerable cell that can regenerate into a new plant of the invention.

The invention further relates to plant tissue of a plant of the invention, which may comprise the CNV of the 9-LOX5 gene of the invention. The tissue can be undifferentiated tissue or already differentiated tissue. Undifferentiated tissue is for example a stem tip, an anther, a petal, or pollen, and can be used in micropropagation to obtain new plantlets that are grown into new plants of the invention. The tissue can also be grown from a cell of the invention.

The invention moreover relates to progeny of a plant, a cell, a tissue, or a seed of the invention, which progeny may comprise the CNV of the 9-LOX5 gene of the invention. Such progeny can in itself be a plant, a cell, a tissue, or a seed.

The present invention will be further illustrated in the Examples that follow that are for illustration purposes only and are not intended to limit the invention in any way. In the description and the Examples reference is made to the below figures.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Identification of Copy Number Variation (CNV) of 9-LOX5

Research on powdery mildew resistance determined that in watermelon (*Citrullus lanatus*) a region on chromosome 2 that has a large number of LOX genes arranged in a tandem gene array was involved in powdery mildew resistance. A genotyping-by-sequencing (GBS) approach including 96 individual plants was set-up to get more insight in the region of interest. It was observed that a clearly delineated stretch of DNA within the region had an unexpectedly high number of heterozygous SNPs. The subsequent use of a visualization tool for the NGS data that were generated showed that in addition the average number of reads, i.e. the readdepth, in this stretch appeared to be doubled as compared to the regions surrounding it (FIG. 4). Using this outcome, it was finally established that a copy number variation (CNV) had to be involved in the powdery mildew resistance.

Further research on this CNV region determined that the length of the CNV region varied between different genotypes (FIG. 6) An in-depth analysis however established that there was one overlapping gene that was present in all genomes of powdery mildew resistant genotypes having the CNV. It was further concluded that this gene, responsible for the powdery mildew resistance, could be annotated as a 9-LOX5 gene.

Resequencing of the CNV region in the available germplasm led to a further interesting find. Two alleles of the gene could be identified, designated 9-LOX5_1, which comprises SEQ ID NO: 1, and 9-LOX5_2, which comprises SEQ ID NO: 3, which alleles were present in the CNV in different combinations: two 9-LOX5_1 alleles, two 9-LOX5_2 alleles, one allele of each, but also three or four copies of the 9-LOX5_2 allele could be present. Both alleles could also be found independently as a single copy. Since there were quite a large number of SNPs present between the alleles, it was decided that it needed to be studied whether the presence of certain SNPs was related to the resistance, or indeed the presence of a copy number variation as such, i.e. the multiple copies of the gene on the same chromosome.

Example 2: 9-LOX5 CNV Presence in Relation to Powdery Mildew Resistance

Figure 6:
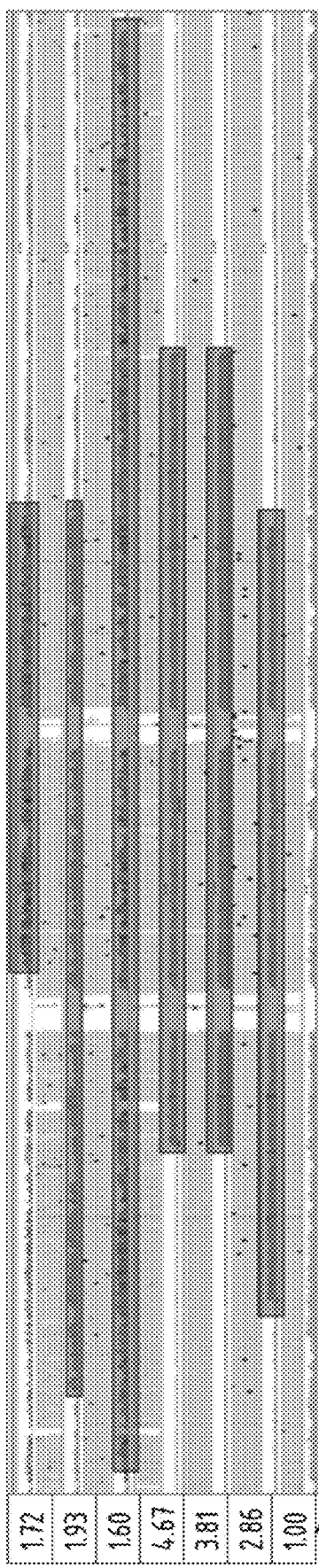

Thirteen different lines having the 9-LOX5 CNV in different allele combinations, or having only a single copy of one of the 9-LOX5 alleles, were phenotyped for powdery mildew resistance using the method as described in Example 4. The presence of the alleles was determined using resequencing data; also the total length of the CNV region could be established in this way (FIG. 6).

The results are presented in Table 1. Columns 2 and 3 indicate the number of copies of a certain 9-LOX5 allele that is present on the same chromosome. All included lines were homozygous, so both chromosomes have the same number of copies. All R lines are internal breeding material, two of which have been deposited. All included S lines are publicly available and can be used as susceptible controls.

TABLE 1

Presence of 9-LOX5 alleles in relation to powdery mildew resistance

| | copies of the 9-LOX5_1 allele | copies of the 9-LOX5_2 allele | total 9-LOX5 copies | CNV present | phenotype PM resistance |
|---|---|---|---|---|---|
| NCIMB 43368 | 1 | 1 | 2 | yes | R |
| NCIMB 43508 |   | 2 | 2 | yes | R |
| RZ3378_1 | 2 |   | 2 | yes | R |
| PI296341 | 1 |   | 1 | no | S |
| RZ-900 |   | 1 | 1 | no | S |
| Sugarlee |   | 1 | 1 | no | S |
| RZ3491_47 | 1 | 1 | 2 | yes | R |
| RZ3651_61 | 2 |   | 2 | yes | R |
| RZ3651_62 | 2 |   | 2 | yes | R |
| RZ3651_64 |   | 2 | 2 | yes | R |
| RZ3651_72 |   | 5 | 5 | yes | R |
| RZ3651_73 |   | 4 | 4 | yes | R |
| RZ3651_74 |   | 3 | 3 | yes | R |

The results of the analysis confirmed that the presence of two or more alleles of the 9-LOX5 gene on one chromosome, meaning the presence of a 9-LOX5 CNV, provides powdery mildew resistance. The combination in which the alleles are present has no influence on the resistance. When in total only one copy of the 9-LOX5 gene of the invention in the form of any allele is present on each chromosome, the plant will be susceptible to powdery mildew. The variation between the 9-LOX5 alleles as such was therefore confirmed not to be the cause of the resistance.

Example 3: Reduction of Two 9-LOX5 Copies to 1 Copy Leads to Susceptibility

To be able to follow the presence of an allele in populations derived from the lines in Table 1, markers were developed based on identified SNPs between the copies in the CNV. A score A for a certain marker identifies the presence of 9-LOX52, and score B identifies the presence of 9-LOX5_1. Because in resistant plants copies are present, the marker score of a marker within the CNV in NCIIB 43368 would be AABB, since each chromosome has a copy of the 9-LOX5_1 allele and the 9-LOX5_2 allele within the CNV. The marker score of RZ-900, which is susceptible and has only one copy of the 9-LOX5_2 allele on each chromosome, is AA. A segregating F2 population of a cross between those lines would have plants that show the pattern of either parent, or AAB when heterozygous—one score A from the susceptible parent and score AB from the resistant parent.

However, in a segregating population developed from a cross between the resistant NCIMB 43368 and the susceptible RZ-900, the marker profile of some of the markers in a certain recombinant plant indicated that only the 9-LOX51 allele was present, i.e. there was a BB score. This was a completely unexpected result, since no chromosome was present in either parent that carried only one allele of 9-LOX5_1.

To find out the cause of this observation, resequencing of the recombinant was done. This showed that a recombination event had taken place within the CNV, whereby the first part of the 9-LOX51 allele was recombined with the last part of the 9-LOX5_2 allele. The center part of the CNV region, which comprises the last part of the 9-LOX_1 allele and the first part of the 9-LOX5_2 allele, was thereby deleted through this recombination event. This resulted in the presence of only one allele, 9-LOX5_3, which was a new allele made up of two halves of the already present alleles (FIG. 3; SEQ ID NO: 5 and SEQ ID NO: 6).

Subsequently, phenotyping of this recombinant was done as well, and it showed to be susceptible to powdery mildew. By being able to delete essentially one of the alleles in the CNV, which led to a change from resistant to susceptible, it was further confirmed that the presence of multiple 9-LOX5 copies provides powdery mildew resistance and the presence of only one copy leads to susceptibility.

Example 4: Bio-Assay for Powdery Mildew Resistance Using a Leaf-Disc Method

Determining resistance of a watermelon line can be done very efficiently by using a leaf-disc assay. Field or greenhouse observations are alternative options, but take more time and space, and they cannot be carried out in all seasons. The correlation between the field or greenhouse methods and the leaf-disc assay was analysed, and it was found that there was a very good correlation. This makes the leaf-disc assay the preferred method for determining resistance.

For the leaf-disc assay, after sowing of the seeds leaf-discs of around 1.5 cm in diameter are taken when the plants are at two true-leaf stage. Each leaf-disc is placed in a box of around 18×12 cm, wherein for example 32 discs can be combined. Each leaf-disc represents one plant. Susceptible controls are included, at least one disc per box, and if available, also one or more discs of one or more resistant controls.

To prepare the inoculum, watermelon plants are grown under nursery conditions, meaning under 25° C./18° C. day/night temperature. At cotyledon stage they are infected by brushing powdery mildew spores onto the cotyledons. After that they are kept for 10-12 days in a phytotron chamber at 22° C. day and 20° C. night temperature, under 12/12 hours light/dark conditions. After 10-12 days the inoculum is ready to be used.

The box is inoculated the day after taking the leaf discs by blowing air from the well-infected watermelon cotyledons onto the leaf-discs that are to be tested. The boxes are kept in a phytotron chamber at 22° C. day and 20° C. night temperature, under 12/12 hours light/dark conditions. Scoring is done after 10-12 days; to determine the optimum moment, it should be checked if the susceptible controls are indeed showing sufficient symptoms.

Scoring is done according to the symptoms as presented in Table 2.

TABLE 2

Scoring powdery mildew symptoms

| Score | Powdery mildew symptom description | Type of resistance |
|---|---|---|
| 1 | No symptoms | R |
| 2 | Some isolated spots, <10% of the surface | R |
| 3 | Thin spots on 25% to 50% of the surface, like voile | IR |
| 4 | Thick spots | S |
| 5 | Some sporulation, slightly white | S |
| 6 | Some - medium sporulation | S |
| 7 | Medium sporulation, white | S |
| 8 | Medium - heavy sporulation | S |
| 9 | Very heavy sporulation, very white | S |

Scores 1 and 2 are categorized to be resistant (R). Score 3 is categorized to be intermediate resistant (IR), which is a lower level of resistance. Scores 4-9 are for susceptible plants (S).

The invention is further described by the following numbered paragraphs:

1. Plant comprising a copy number variation (CNV) of a 9-LOX5 gene, which CNV comprises at least 2 copies of a 9-LOX5 gene on the same chromosome, wherein the 9-LOX5 gene comprises SEQ ID NO: 1, or a sequence having at least 60% sequence identity to SEQ ID NO: 1, and wherein the presence of the CNV leads to powdery mildew resistance in the plant.

2. Plant of paragraph 1, wherein the copies of the 9-LOX5 gene in the CNV comprise different alleles.

3. Plant of paragraph 1 or 2, wherein the CNV comprises multiple copies of the 9-LOX5_1 allele comprising SEQ ID NO: 1.

4. Plant of paragraph 1 or 2, wherein the CNV comprises multiple copies of the 9-LOX5_2 allele comprising SEQ ID NO: 3.

5. Plant of any of the paragraphs 1-4, wherein the CNV comprises one or more copies of the 9-LOX5_1 allele comprising SEQ ID NO: 1, and one or more copies of the 9-LOX5_2 allele comprising SEQ ID NO: 3.

6. Plant of any of the paragraphs 1-5 which is a plant of the family Cucurbitaceae, preferably a plant of the species *Citrullus lanatus, Cucumis sativus, Cucumis melo, Cucurbita pepo*, or *Cucurbita moschata*.

7. Plant of paragraph 6 which is a *Citrullus lanatus* plant.

8. Nucleic acid molecule comprising two or more copies of SEQ ID NO: 1 or of a sequence having at least 60% identity thereto, or two or more copies of SEQ ID NO: 3 or of a sequence having at least 60% identity thereto.

9. Nucleic acid molecule comprising one or more copies of SEQ ID NO: 1 or of a sequence having at least 60% identity thereto, and one or more copies of SEQ ID NO: 3 or of a sequence having at least 60% identity thereto.

10. Method for producing a plant that is resistant to powdery mildew comprising introducing a copy number variation (CNV) of a 9-LOX5 gene comprising multiple copies of one or more 9-LOX5 alleles on the same chromosome into a plant.

11. Method for selecting a powdery mildew resistant plant comprising determining the presence of a CNV of a 9-LOX5 gene comprising multiple copies of one or more 9-LOX5 alleles on the same chromosome, and selecting a plant comprising said CNV of the 9-LOX5 gene as a powdery mildew resistant plant.

12. Powdery mildew resistant plant obtained by a method of paragraph 10 or 11.

13. Seed comprising the nucleotide sequence of paragraph 8 or paragraph 9.

14. Part of a plant of any of the paragraphs 1-7 or in paragraph 12, which part of a plant comprises a CNV of a 9-LOX5 gene comprising multiple copies of one or more 9-LOX5 alleles.

15. Part of a plant of paragraph 14, wherein the part is a fruit.

16. Part of a plant of paragraph 15, wherein the plant is *Citrullus lanatus* and the fruit is a red fleshed *Citrullus lanatus* fruit.

17. Propagation material suitable for producing a plant of any of the paragraphs 1-7 or in paragraph 12, wherein the propagation material comprises a CNV of a 9-LOX5 gene comprising multiple copies of one or more 9-LOX5 alleles.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An agronomically elite *Citrullus lanatus* plant that produces fruits with red flesh comprising a copy number variation (CNV) of a 9-LOX5 gene,
   which CNV comprises at least 2 copies of a 9-LOX5 gene on the same chromosome,
   wherein the 9-LOX5 gene comprises:
      one or more copies of a 9-LOX5_1 allele having the sequence of SEQ ID NO: 1 or a sequence having at least 99% sequence identity to SEQ ID NO: 1, and/or
      one or more copies of a 9-LOX5_2 allele having the sequence of SEQ ID NO: 3 or a sequence having at least 99% sequence identity to SEQ ID NO: 3,
   wherein the presence of the CNV leads to resistance to at least *Podosphaera xanthii* in the agronomically elite plant.

2. The agronomically elite plant of claim 1, wherein the CNV comprises multiple copies of the 9-LOX5_1 allele having the sequence of SEQ ID NO: 1, or a sequence having at least 99% sequence identity to SEQ ID NO: 1.

3. The agronomically elite plant of claim 1, wherein the CNV comprises multiple copies of the 9-LOX5_2 allele having the sequence of SEQ ID NO: 3, or a sequence having at least 99% sequence identity to SEQ ID NO: 3.

4. A method for producing an agronomically elite *Citrullus lanatus* plant that is resistant to at least *Podosphaera xanthii* and that produces fruits with red flesh, said method comprising:
   introducing into a *Citrullus lanatus* plant that produces fruits with red flesh a copy number variation (CNV) of a 9-LOX5 gene,
   which CNV comprises at least 2 copies of a 9-LOX5 gene on the same chromosome,
   wherein the 9-LOX5 gene comprises:
      one or more copies of a 9-LOX5_1 allele having the sequence of SEQ ID NO: 1 or a sequence having at least 99% sequence identity to SEQ ID NO: 1, and/or
      one or more copies of a 9-LOX5_2 allele having the sequence of SEQ ID NO: 3 or a sequence having at least 99% sequence identity to SEQ ID NO: 3,
      wherein the presence of the CNV leads to resistance to at least *Podosphaera xanthii* in the agronomically elite plant,
   whereby there is producing of the agronomically elite *Citrullus lanatus* plant that is resistant to at least *Podosphaera xanthii* and that produces fruits with red flesh.

5. A method for selecting a *Citrullus lanatus* plant that is resistant to at least *Podosphaera xanthii* and that produces fruits with red flesh comprising:

determining in a *Citrullus lanatus* plant that produces fruits with red flesh the presence of a copy number variation (CNV) of a 9-LOX5 gene, which CNV comprises at least 2 copies of a 9-LOX5 gene on the same chromosome, wherein the 9-LOX5 gene comprises:

one or more copies of a 9-LOX5_1 allele having the sequence of SEQ ID NO: 1 or a sequence having at least 99% sequence identity to SEQ ID NO: 1, and/or one or more copies of a 9-LOX5_2 allele having the sequence of SEQ ID NO: 3 or a sequence having at least 99% sequence identity to SEQ ID NO: 3, wherein the presence of the CNV leads to resistance to at least *Podosphaera xanthii* in the plant, and selecting the *Citrullus lanatus* plant that produces fruits with red flesh and that from the determining step comprises said CNV of the 9-LOX5 gene, whereby there is selecting of the *Citrullus lanatus* plant that is resistant to at least *Podosphaera xanthii* and produces fruits with red flesh.

6. An agronomically elite *Citrullus lanatus* plant that is resistant to at least *Podosphaera xanthii* and that produces fruits with red flesh, obtained by the method of claim 4.

7. A *Citrullus lanatus* plant that is resistant to at least *Podosphaera xanthii* and that produces fruits with red flesh, obtained by the method of claim 5, wherein in the method there is the selecting of an agronomically elite *Citrullus lanatus* plant that is resistant to at least *Podosphaera xanthii* and produces fruits with red flesh.

8. An agronomically elite *Citrullus lanatus* seed comprising two or more copies of SEQ ID NO: 1 or of a sequence having at least 99% sequence identity thereto, or two or more copies of SEQ ID NO: 3 or of a sequence having at least 99% sequence identity thereto.

9. An agronomically elite *Citrullus lanatus* seed comprising one or more copies of SEQ ID NO: 1 or of a sequence having at least 99% sequence identity thereto, and one or more copies of SEQ ID NO: 3 or of a sequence having at least 99% sequence identity thereto.

10. A part of the agronomically elite plant of claim 1, comprising the CNV.

11. A propagation material suitable for producing the agronomically elite plant of claim 1, wherein the propagation material comprises the CNV.

12. The agronomically elite plant of claim 1, wherein the 9-LOX5_1 allele has the sequence of SEQ ID NO: 1 and the 9-LOX5_2 allele has the sequence of SEQ ID NO: 3.

13. The agronomically elite plant of claim 1, wherein the 9-LOX5_1 allele has the sequence of SEQ ID NO: 1.

14. The agronomically elite plant of claim 1, wherein the 9-LOX5_2 allele has the sequence of SEQ ID NO: 3.

15. The agronomically elite plant of claim 1, wherein the plant is resistant to *Podosphaera xanthii* races 1W and 2W.

16. The agronomically elite plant of claim 1, wherein the plant is additionally resistant to *Golovinomyces cichoracearum*.

17. A part of the agronomically elite plant of claim 6 comprising the CNV.

18. A propagation material suitable for producing the agronomically elite plant of claim 6, wherein the propagation material comprises the CNV.

19. A part of the plant of claim 7 comprising the CNV.

20. A propagation material suitable for producing the plant of claim 7, wherein the propagation material comprises the CNV.

* * * * *

```
                           SEQUENCE LISTING

<160> NUMBER OF SEQ ID NOS: 6

<210> SEQ ID NO 1
<211> LENGTH: 2400
<212> TYPE: DNA
<213> ORGANISM: Citrullus lanatus
<220> FEATURE:
<223> OTHER INFORMATION: 9-LOX5_1 allele - coding sequence

<400> SEQUENCE: 1
atggttaaag ggaaagttac tttgtccaga agcaattgga tcaataggcc aaaactaaaa      60
cttaccctac aactcatcag ctctgtgaag tgtgatccat caataggaaa gcaagggaaa     120
catggaaaga aaatatactt gcaaaatgaa ggagatgcaa ataatgaagg ggaaagagtg     180
tttagtgtga gttttgattg ggatgaagag attgggaatc caggagctat cttggtaaga     240
aacaaccatc gttttcaag attcttcctc aaatctatta ctcttttga tctacctgcc      300 ttcggaaaca tccactttga ttgcaactct tggattcacc ctaatagaca tacacataca     360
gatcatcaca ttttctttgt aaataaggca tatcttcctc atgagacacc agagccactt     420
caaaattata gagagaaaga actcgaaaaa agagaggag atggtagaag agtgcctaaa      480
aattgggaaa acatatacga ctatgatgtc tacaatgata ttagtgattt agattctaat     540
tcaacaaata aacccctat tcttggagga ttggtgcctt atccacgtag aggaagaact      600
ggacgaccac gctcaaaaaa agatgataga tatgagacca gatgtgcaat caaagatgtt     660
tatgttccca gtgatgaaag atttagtgac ttgaagaaat cagatttga tattcatgga     720 ttaagatcag tgcttcgaga cattaaagat aaacttaaag cttcattagg aaaatctcct     780
aaaagattgg agtctcttaa agatgtgtat gcaatctatg aaccacgttc cttctttcga     840
cgagggaaat ttctaatgcc ccaggtgatc gaaggtaata atctggatg gaggactgat      900 gaagagttcg ctagagaaat gttggcagga gtaaatccta tggtcattcg tcgtctccaa     960
agtttcccac cgactagcaa ccttaaccct agtgattatg gtgatcaaaa cagcaagata    1020
acaccaaaac agattatgaa tggtatggag ggacttacgg tagaccaggc aattgcagaa    1080
aacaagctgt acatattaga tcaccatgat ttaataattc catatcttaa aagaataaat    1140
acaacttcca caaaaactta tgctacaaga acacttctct tcctaaaaaa tgatgggact    1200
ttgaagcctt tagcaattga attgagcttg ccacaccctc aaggatacca atttggagcc    1260
attagtaaaa tattgttgcc agacaaagga agaattgggg aaccactttg gcaactagct    1320
aaagcttatg ttgttgtcaa tgactctggt caccatcaac tcatcagcca ctggctaaac    1380
acacatgccg taattgagcc atttgtgatt gcaacacata gacaactcag tgttgttcat    1440
ccgattcaca agttgcttgt tcctcacttt cgatacacca tgaagatcaa tgctcttgca    1500
agatcaaccc tcattaatac tgatggtatt attgagaaaa ctcaatatcc ttctaagtat    1560
tctatggaga tgtcttcttt tgcttatcaa aattgggact ttactcaaca agcactccct    1620
gctgacctaa tcaagagagg aattgcaatt gaagatccaa gtgccccaca tggactccaa    1680
ttactcataa aagattatcc atatgctgtt gatggacttg acatttgggc agccatcaaa    1740
acatgggtac gagagtattg ttcaatttac tacaagaatg atgaaatgat ttgtaatgat    1800
ccagagctca aatcatggtg gaatgaagtt cgagaaagag gccatgaaga caagaaagac    1860
```

```
gaaccatggt ggccaaaaat gcaaagtatt gaagagctaa tcaatagttg caccatcatc    1920
atatggattt ctcggctct tcatgctgca gttaactttg ggcaatatcc ttacggtggt    1980
tttcttccta atcgcccatc gactagcgta cgattcttac cggaagaagg cacatctgag    2040
tatctagaac tgcagtcaaa tacagataaa gctttcttga aaacattcac ttccgaacta    2100
caagaaaatg atcttctgaa tatcactaca attcaacttt tatcctcaca ttctcttgat    2160
gagtcctatt tagggcaaag aaatgatcca aactggactt ttgataagaa tgctttagat    2220
gcatttgaga atttcaaaag aaagttagtt gaaattgggg aaatgattgg gaaaagaaac    2280
caagatcata tgttgaagaa tcgagttgga cgagaggtga agatgacata cactttgcta    2340
cttcccacta gtcaacctgg cgttacatgt cgaggaattc ccaatagcat ttctatttga    2400
```

<210> SEQ ID NO 2
<211> LENGTH: 799
<212> TYPE: PRT
<213> ORGANISM: Citrullus lanatus
<220> FEATURE:
<223> OTHER INFORMATION: 9-LOX5_1 allele - protein sequence

<400> SEQUENCE: 2

```
Met Val Lys Gly Lys Val Thr Leu Ser Arg Ser Asn Trp Ile Asn Arg
1               5                   10                  15

Pro Lys Leu Lys Leu Thr Leu Gln Leu Ile Ser Ser Val Lys Cys Asp
            20                  25                  30

Pro Ser Ile Gly Lys Gln Gly Lys His Gly Lys Lys Ile Tyr Leu Gln
        35                  40                  45

Asn Glu Gly Asp Ala Asn Glu Gly Glu Arg Val Phe Ser Val Ser
    50                  55                  60

Phe Asp Trp Asp Glu Glu Ile Gly Asn Pro Gly Ala Ile Leu Val Arg
65                  70                  75                  80

Asn Asn His Arg Phe Ser Arg Phe Phe Leu Lys Ser Ile Thr Leu Phe
                85                  90                  95

Asp Leu Pro Ala Phe Gly Asn Ile His Phe Asp Cys Asn Ser Trp Ile
            100                 105                 110

His Pro Asn Arg His Thr His Thr Asp His His Ile Phe Phe Val Asn
        115                 120                 125

Lys Ala Tyr Leu Pro His Glu Thr Pro Glu Pro Leu Gln Asn Tyr Arg
    130                 135                 140

Glu Lys Glu Leu Glu Lys Lys Arg Gly Asp Gly Arg Arg Val Pro Lys
145                 150                 155                 160

Asn Trp Glu Asn Ile Tyr Asp Tyr Asp Val Tyr Asn Asp Ile Ser Asp
                165                 170                 175

Leu Asp Ser Asn Ser Thr Asn Lys Pro Pro Ile Leu Gly Gly Leu Val
            180                 185                 190

Pro Tyr Pro Arg Arg Gly Arg Thr Gly Arg Pro Arg Ser Lys Lys Asp
        195                 200                 205

Asp Arg Tyr Glu Thr Arg Cys Ala Ile Lys Asp Val Tyr Val Pro Ser
    210                 215                 220

Asp Glu Arg Phe Ser Asp Leu Lys Lys Ser Asp Phe Asp Ile His Gly
225                 230                 235                 240

Leu Arg Ser Val Leu Arg Asp Ile Lys Asp Lys Leu Lys Ala Ser Leu
                245                 250                 255

Gly Lys Ser Pro Lys Arg Leu Glu Ser Leu Lys Asp Val Tyr Ala Ile
            260                 265                 270
```

Tyr Glu Pro Arg Ser Phe Phe Arg Arg Gly Lys Phe Leu Met Pro Gln
            275                 280                 285

Val Ile Glu Gly Asn Lys Ser Gly Trp Arg Thr Asp Glu Glu Phe Ala
290                 295                 300

Arg Glu Met Leu Ala Gly Val Asn Pro Met Val Ile Arg Arg Leu Gln
305                 310                 315                 320

Ser Phe Pro Pro Thr Ser Asn Leu Asn Pro Ser Asp Tyr Gly Asp Gln
                325                 330                 335

Asn Ser Lys Ile Thr Pro Lys Gln Ile Met Asn Gly Met Glu Gly Leu
            340                 345                 350

Thr Val Asp Gln Ala Ile Ala Glu Asn Lys Leu Tyr Ile Leu Asp His
        355                 360                 365

His Asp Leu Ile Ile Pro Tyr Leu Lys Arg Ile Asn Thr Thr Ser Thr
    370                 375                 380

Lys Thr Tyr Ala Thr Arg Thr Leu Leu Phe Leu Lys Asn Asp Gly Thr
385                 390                 395                 400

Leu Lys Pro Leu Ala Ile Glu Leu Ser Leu Pro His Pro Gln Gly Tyr
                405                 410                 415

Gln Phe Gly Ala Ile Ser Lys Ile Leu Leu Pro Asp Lys Gly Arg Ile
            420                 425                 430

Gly Glu Pro Leu Trp Gln Leu Ala Lys Ala Tyr Val Val Asn Asp
        435                 440                 445

Ser Gly His His Gln Leu Ile Ser His Trp Leu Asn Thr His Ala Val
    450                 455                 460

Ile Glu Pro Phe Val Ile Ala Thr His Arg Gln Leu Ser Val Val His
465                 470                 475                 480

Pro Ile His Lys Leu Leu Val Pro His Phe Arg Tyr Thr Met Lys Ile
                485                 490                 495

Asn Ala Leu Ala Arg Ser Thr Leu Ile Asn Thr Asp Gly Ile Ile Glu
            500                 505                 510

Lys Thr Gln Tyr Pro Ser Lys Tyr Ser Met Glu Met Ser Ser Phe Ala
        515                 520                 525

Tyr Gln Asn Trp Asp Phe Thr Gln Gln Ala Leu Pro Ala Asp Leu Ile
    530                 535                 540

Lys Arg Gly Ile Ala Ile Glu Asp Pro Ser Ala Pro His Gly Leu Gln
545                 550                 555                 560

Leu Leu Ile Lys Asp Tyr Pro Tyr Ala Val Asp Gly Leu Asp Ile Trp
                565                 570                 575

Ala Ala Ile Lys Thr Trp Val Arg Glu Tyr Cys Ser Ile Tyr Tyr Lys
            580                 585                 590

Asn Asp Glu Met Ile Cys Asn Asp Pro Glu Leu Lys Ser Trp Trp Asn
        595                 600                 605

Glu Val Arg Glu Arg Gly His Glu Asp Lys Lys Asp Glu Pro Trp Trp
    610                 615                 620

Pro Lys Met Gln Ser Ile Glu Glu Leu Ile Asn Ser Cys Thr Ile Ile
625                 630                 635                 640

Ile Trp Ile Ser Ser Ala Leu His Ala Ala Val Asn Phe Gly Gln Tyr
                645                 650                 655

Pro Tyr Gly Gly Phe Leu Pro Asn Arg Pro Ser Thr Ser Val Arg Phe
            660                 665                 670

Leu Pro Glu Glu Gly Thr Ser Glu Tyr Leu Glu Leu Gln Ser Asn Thr
        675                 680                 685

Asp Lys Ala Phe Leu Lys Thr Phe Thr Ser Glu Leu Gln Glu Asn Asp

```
                   690                  695                  700
Leu Leu Asn Ile Thr Thr Ile Gln Leu Leu Ser Ser His Ser Leu Asp
705                     710                  715                  720

Glu Ser Tyr Leu Gly Gln Arg Asn Asp Pro Asn Trp Thr Phe Asp Lys
                725                  730                  735

Asn Ala Leu Asp Ala Phe Glu Asn Phe Lys Arg Lys Leu Val Glu Ile
                740                  745                  750

Gly Glu Met Ile Gly Lys Arg Asn Gln Asp His Met Leu Lys Asn Arg
                755                  760                  765

Val Gly Arg Glu Val Lys Met Thr Tyr Thr Leu Leu Leu Pro Thr Ser
                770                  775                  780

Gln Pro Gly Val Thr Cys Arg Gly Ile Pro Asn Ser Ile Ser Ile
785                     790                  795
```

<210> SEQ ID NO 3
<211> LENGTH: 2400
<212> TYPE: DNA
<213> ORGANISM: Citrullus lanatus
<220> FEATURE:
<223> OTHER INFORMATION: 9-LOX5_2 allele - coding sequence

<400> SEQUENCE: 3

```
atggttaaag ggaaagttac tttgtccaga agcaattgga tgaataggcc aaaactaaaa    60
cttaccctac aactcatcag ctctgtcaag ggtgatccat caatagaaat gcaggggaaa   120
catggaaaga aatatactt gcaaaatgaa ggagatgcaa ataatgaagg ggaaagagtg    180
tttagtgtga gttttgattg ggatgaagag attgggaatc caggagctat cttggtaaga   240
aacaaccatc gttttcaag attcttcctc aaatctatta ctcttttga tgtacctgcc    300
ttcggaaaca tccactttga ttgcaactct tggattcacc ctaatagaca tacacataca   360
gatcatcaca ttttctttgt aaataaggca tatcttcctc atgagacacc agagccactt   420
aaaatgtata gagagaaaga actcgaaaaa aagagaggaa atggtagaag agtgcctaaa   480
aattgggaaa acatatacga ctatgatgtc tacaatgata ttagtgattt agattctaat   540
tcaacaaata aaccccctat tcttggagga ttagtgcctt atccacgcag aggaagaact   600
ggacgaccat gcttacaaaa tgatgataga tatgagacca gatgtgcaat caaagatgtt   660
tatgttccca gtgatgaaag attagtgac ttgaagaaat cagattttga tattcatgga   720
ttaagatcag tgcttcgaga cattaaagat aaacttaaag cttcattagg aaaatctcct   780
aaaagattgg agtctcttaa agatgtgtat gcaatctatg aaccacgttc cttctttcga   840
cgagggaaat ttccaatgcc ccaggtgatc gaaggtaata atctggatgg aggactgat    900
gaagagttcg ctagagaaat gttggcagga gtaaatccta tggtcattcg tcgtctccaa   960
agtttcccac cgactagcaa ccttaaccct agtgactatg gtgatcaaaa cagcaagata  1020
acaccaaaac agattatgaa tggtatggag ggacttacgg tagaccaggc aattgcagaa  1080
aacaagctgt acatattaga tcaccatgat ttaataattc catatcttaa agaataaat  1140
acaacttcca caaaaactta tgctacaaga acacttctct tcctaaaaaa tgatgggact  1200
ttgaagcctt tagcaattga attgagcttg ccacaccctc aaggatacca atttggagcc  1260
attagtaaaa tattgttgcc agataaagga aaaattgggg aaccacttg gcaactagct  1320
aaagcttatg ttgttgtcaa tgactctggt caccatcaac tcatcagcca ctggctaaac  1380
acacatgccg taattgagcc atttgtgatt gcaacacata gacaactcag tgttgttcat  1440
ccgattcaca agttgcttgt tcctcacttt cgatacacca tgaagatcaa tgctcttgca  1500
```

```
agatcaaccc tcattaatac tgatggtatt attgagaaaa ctcaatatcc ttctaagtat    1560
tctatggaga tgtcttcttt tgcttatcaa aattgggacc ttactcaaca agcactccct    1620
gctgacctaa tcaagagagg aattgcaatt gaagatccaa gtgccccaca tggactccaa    1680
ttactcataa aagattatcc atatgctgtt gatggacttg acatttggac agccatcaaa    1740
acatgggtac gagagtattg ttcaatttac tacaagaacg atgaaatgat tcgtaatgat    1800
ccagagctca atcatggtg gaatgaagtt cgagaaagag gccatgaaga caagaaagac    1860
gaaccatggt ggccaaaaat gcaaagtatt gaagagctaa tcaatagttg caccatcatc    1920
atatggattt cttcggctct tcatgctgca gttaactttg gcaatatcc ttacggtggt    1980 tttcttccta atcgcccatc gactagcgta cgattcttac cggaagaagg cacatctgag    2040
tatctagaac tgcagtcaaa tacagataaa gctttcttga aacattcac ttccgaacta    2100 caagaaaatg atcttctgaa tatcactaca attcaacttt tatcctcaca ttctcttgat    2160
gagtcctatt tagggcaaag aagtgatccg aactggactt tgataagaa tgctttagat    2220 gcatttgaga atttcaaaag aaagttagtt gaaattgggg aaatgattgg gaaaagaaac    2280
aaagatgata tgttgaagaa tcgagctgga cgagaggtga agatgacata cactttgcta    2340
cttcccacta gtcaacctgg cattacatgt cgaggaattc ccaatagcat ttctatttga    2400
```

<210> SEQ ID NO 4
<211> LENGTH: 799
<212> TYPE: PRT
<213> ORGANISM: Citrullus lanatus
<220> FEATURE:
<223> OTHER INFORMATION: 9-LOX5_2 allele - protein sequence

<400> SEQUENCE: 4

```
Met Val Lys Gly Lys Val Thr Leu Ser Arg Ser Asn Trp Met Asn Arg
1               5                   10                  15

Pro Lys Leu Lys Leu Thr Leu Gln Leu Ile Ser Ser Val Lys Gly Asp
            20                  25                  30

Pro Ser Ile Glu Met Gln Gly Lys His Gly Lys Lys Ile Tyr Leu Gln
        35                  40                  45

Asn Glu Gly Asp Ala Asn Asn Glu Gly Glu Arg Val Phe Ser Val Ser
    50                  55                  60

Phe Asp Trp Asp Glu Glu Ile Gly Asn Pro Gly Ala Ile Leu Val Arg
65                  70                  75                  80

Asn Asn His Arg Phe Ser Arg Phe Phe Leu Lys Ser Ile Thr Leu Phe
                85                  90                  95

Asp Val Pro Ala Phe Gly Asn Ile His Phe Asp Cys Asn Ser Trp Ile
            100                 105                 110

His Pro Asn Arg His Thr His Thr Asp His His Ile Phe Phe Val Asn
        115                 120                 125

Lys Ala Tyr Leu Pro His Glu Thr Pro Glu Pro Leu Lys Met Tyr Arg
    130                 135                 140

Glu Lys Glu Leu Glu Lys Lys Arg Gly Asn Gly Arg Arg Val Pro Lys
145                 150                 155                 160

Asn Trp Glu Asn Ile Tyr Asp Tyr Asp Val Tyr Asn Asp Ile Ser Asp
                165                 170                 175

Leu Asp Ser Asn Ser Thr Asn Lys Pro Pro Ile Leu Gly Gly Leu Val
            180                 185                 190

Pro Tyr Pro Arg Arg Gly Arg Thr Gly Arg Pro Cys Leu Gln Asn Asp
        195                 200                 205
```

```
Asp Arg Tyr Glu Thr Arg Cys Ala Ile Lys Asp Val Tyr Val Pro Ser
    210                 215                 220

Asp Glu Arg Phe Ser Asp Leu Lys Lys Ser Asp Phe Asp Ile His Gly
225                 230                 235                 240

Leu Arg Ser Val Leu Arg Asp Ile Lys Asp Lys Leu Lys Ala Ser Leu
                245                 250                 255

Gly Lys Ser Pro Lys Arg Leu Glu Ser Leu Lys Asp Val Tyr Ala Ile
                260                 265                 270

Tyr Glu Pro Arg Ser Phe Phe Arg Arg Gly Lys Phe Pro Met Pro Gln
            275                 280                 285

Val Ile Glu Gly Asn Lys Ser Gly Trp Arg Thr Asp Glu Glu Phe Ala
    290                 295                 300

Arg Glu Met Leu Ala Gly Val Asn Pro Met Val Ile Arg Arg Leu Gln
305                 310                 315                 320

Ser Phe Pro Pro Thr Ser Asn Leu Asn Pro Ser Asp Tyr Gly Asp Gln
                325                 330                 335

Asn Ser Lys Ile Thr Pro Lys Gln Ile Met Asn Gly Met Glu Gly Leu
                340                 345                 350

Thr Val Asp Gln Ala Ile Ala Glu Asn Lys Leu Tyr Ile Leu Asp His
            355                 360                 365

His Asp Leu Ile Ile Pro Tyr Leu Lys Arg Ile Asn Thr Thr Ser Thr
370                 375                 380

Lys Thr Tyr Ala Thr Arg Thr Leu Leu Phe Leu Lys Asn Asp Gly Thr
385                 390                 395                 400

Leu Lys Pro Leu Ala Ile Glu Leu Ser Leu Pro His Pro Gln Gly Tyr
                405                 410                 415

Gln Phe Gly Ala Ile Ser Lys Ile Leu Leu Pro Asp Lys Gly Lys Ile
            420                 425                 430

Gly Glu Pro Leu Trp Gln Leu Ala Lys Ala Tyr Val Val Asn Asp
            435                 440                 445

Ser Gly His His Gln Leu Ile Ser His Trp Leu Asn Thr His Ala Val
    450                 455                 460

Ile Glu Pro Phe Val Ile Ala Thr His Arg Gln Leu Ser Val Val His
465                 470                 475                 480

Pro Ile His Lys Leu Leu Val Pro His Phe Arg Tyr Thr Met Lys Ile
                485                 490                 495

Asn Ala Leu Ala Arg Ser Thr Leu Ile Asn Thr Asp Gly Ile Ile Glu
                500                 505                 510

Lys Thr Gln Tyr Pro Ser Lys Tyr Ser Met Glu Met Ser Ser Phe Ala
            515                 520                 525

Tyr Gln Asn Trp Asp Leu Thr Gln Gln Ala Leu Pro Ala Asp Leu Ile
    530                 535                 540

Lys Arg Gly Ile Ala Ile Glu Asp Pro Ser Ala Pro His Gly Leu Gln
545                 550                 555                 560

Leu Leu Ile Lys Asp Tyr Pro Tyr Ala Val Asp Gly Leu Asp Ile Trp
                565                 570                 575

Thr Ala Ile Lys Thr Trp Val Arg Glu Tyr Cys Ser Ile Tyr Tyr Lys
            580                 585                 590

Asn Asp Glu Met Ile Arg Asn Asp Pro Glu Leu Lys Ser Trp Trp Asn
            595                 600                 605

Glu Val Arg Glu Arg Gly His Glu Asp Lys Lys Asp Glu Pro Trp Trp
610                 615                 620
```

```
Pro Lys Met Gln Ser Ile Glu Glu Leu Ile Asn Ser Cys Thr Ile Ile
625                 630                 635                 640

Ile Trp Ile Ser Ser Ala Leu His Ala Ala Val Asn Phe Gly Gln Tyr
            645                 650                 655

Pro Tyr Gly Gly Phe Leu Pro Asn Arg Pro Ser Thr Ser Val Arg Phe
                660                 665                 670

Leu Pro Glu Glu Gly Thr Ser Glu Tyr Leu Glu Leu Gln Ser Asn Thr
            675                 680                 685

Asp Lys Ala Phe Leu Lys Thr Phe Thr Ser Glu Leu Gln Glu Asn Asp
            690                 695                 700

Leu Leu Asn Ile Thr Thr Ile Gln Leu Leu Ser Ser His Ser Leu Asp
705                 710                 715                 720

Glu Ser Tyr Leu Gly Gln Arg Ser Asp Pro Asn Trp Thr Phe Asp Lys
                725                 730                 735

Asn Ala Leu Asp Ala Phe Glu Asn Phe Lys Arg Lys Leu Val Glu Ile
            740                 745                 750

Gly Glu Met Ile Gly Lys Arg Asn Lys Asp Asp Met Leu Lys Asn Arg
            755                 760                 765

Ala Gly Arg Glu Val Lys Met Thr Tyr Thr Leu Leu Leu Pro Thr Ser
770                 775                 780

Gln Pro Gly Ile Thr Cys Arg Gly Ile Pro Asn Ser Ile Ser Ile
785                 790                 795
```

<210> SEQ ID NO 5
<211> LENGTH: 2400
<212> TYPE: DNA
<213> ORGANISM: Citrullus lanatus
<220> FEATURE:
<223> OTHER INFORMATION: 9-LOX5_3 allele - coding sequence

<400> SEQUENCE: 5

```
atggttaaag ggaaagttac tttgtccaga agcaattgga tcaataggcc aaaactaaaa      60
cttaccctac aactcatcag ctctgtgaag tgtgatccat caatagaaat gcagggaaaa     120
catggaaaga aaatatactt gcaaaatgaa ggagatgcaa ataatgaagg ggaaagagtg     180
tttagtgtga gttttgattg ggatgaagag attgggaatc aggagctat cttggtaaga      240
aacaaccatc gttttcaag attcttcctc aaatctatta ctcttttga tgtacctgcc       300
ttcggaaaca tccactttga ttgcaactct tggattcacc taatagaca tacacataca      360
gatcatcaca ttttctttgt aaataaggca tatcttcctc atgagacacc agagccactt     420
aaaatgtata gagagaaaga actcgaaaaa agagaggaa atggtagaag agtgcctaaa      480
aattgggaaa acatatacga ctatgatgtc tacaatgata ttagtgattt agattctaat     540
tcaacaaata aaccccctat tcttggagga ttagtgcctt atccacgcag aggaagaact     600
ggacgaccat gcttacaaaa tgatgataga tatgagacca gatgtgcaat caagatgtt      660
tatgttccca gtgatgaaag atttagtgac ttgaagaaat cagattttga tattcatgga     720
ttaagatcag tgcttcgaga cattaaagat aaacttaaag cttcattagg aaaatctcct     780
aaaagattgg agtctcttaa agatgtgtat gcaatctatg aaccacgttc cttctttcga     840
cgagggaaat ttccaatgcc ccaggtgatc gaagtaata atctggatg gaggactgat       900
gaagagttcg ctagagaaat gttggcagga gtaaatccta tggtcattcg tcgtctccaa     960
agtttcccac cgactagcaa ccttaaccct agtgactatg gtgatcaaaa cagcaagata    1020
acaccaaaac agattatgaa tggtatggag ggacttacgg tagaccaggc aattgcagaa    1080
```

```
aacaagctgt acatattaga tcaccatgat ttaataattc catatcttaa aagaataaat    1140
acaacttcca caaaaactta tgctacaaga acacttctct tcctaaaaaa tgatgggact    1200
ttgaagcctt tagcaattga attgagcttg ccacaccctc aaggatacca atttggagcc    1260
attagtaaaa tattgttgcc agataaagga aaaattgggg aaccactttg caactagct     1320 aaagcttatg ttgttgtcaa tgactctggt caccatcaac tcatcagcca ctggctaaac    1380
acacatgccg taattgagcc atttgtgatt gcaacacata gacaactcag tgttgttcat    1440
ccgattcaca agttgcttgt tcctcacttt cgatacacca tgaagatcaa tgctcttgca    1500
agatcaaccc tcattaatac tgatggtatt attgagaaaa ctcaatatcc ttctaagtat    1560
tctatggaga tgtcttcttt tgcttatcaa aattgggacc ttactcaaca agcactccct    1620
gctgacctaa tcaagagagg aattgcaatt gaagatccaa gtgccccaca tggactccaa    1680
ttactcataa aagattatcc atatgctgtt gatggacttg acatttggac agccatcaaa    1740
acatgggtac gagagtattg ttcaatttac tacaagaacg atgaaatgat tcgtaatgat    1800
ccagagctca atcatggtg gaatgaagtt cgagaaagag gccatgaaga caagaaagac    1860
gaaccatggt ggccaaaaat gcaaagtatt gaagagctaa tcaatagttg caccatcatc    1920
atatggattt cttcggctct tcatgctgca gttaactttg gcaatatcc ttacggtggt     1980 tttcttccta atcgcccatc gactagcgta cgattcttac cggaagaagg cacatctgag    2040
tatctagaac tgcagtcaaa tacagataaa gctttcttga aaacattcac ttccgaacta    2100
caagaaaatg atcttctgaa tatcactaca attcaacttt tatcctcaca ttctcttgat    2160
gagtcctatt tagggcaaag aagtgatccg aactggactt tgataagaa tgctttagat     2220 gcatttgaga atttcaaaag aaagttagtt gaaattgggg aaatgattgg gaaaagaaac    2280
aaagatgata tgttgaagaa tcgagctgga cgagaggtga agatgacata cactttgcta    2340
cttcccacta gtcaacctgg cattacatgt cgaggaattc ccaatagcat ttctatttga    2400
```

<210> SEQ ID NO 6
<211> LENGTH: 799
<212> TYPE: PRT
<213> ORGANISM: Citrullus lanatus
<220> FEATURE:
<223> OTHER INFORMATION: 9-LOX5_3 allele - protein sequence

<400> SEQUENCE: 6

```
Met Val Lys Gly Lys Val Thr Leu Ser Arg Ser Asn Trp Ile Asn Arg
1               5                   10                  15

Pro Lys Leu Lys Leu Thr Leu Gln Leu Ile Ser Val Lys Cys Asp
            20                  25                  30

Pro Ser Ile Glu Met Gln Gly Lys His Gly Lys Lys Ile Tyr Leu Gln
        35                  40                  45

Asn Glu Gly Asp Ala Asn Asn Glu Gly Glu Arg Val Phe Ser Val Ser
    50                  55                  60

Phe Asp Trp Asp Glu Glu Ile Gly Asn Pro Gly Ala Ile Leu Val Arg
65                  70                  75                  80

Asn Asn His Arg Phe Ser Arg Phe Phe Leu Lys Ser Ile Thr Leu Phe
                85                  90                  95

Asp Val Pro Ala Phe Gly Asn Ile His Phe Asp Cys Asn Ser Trp Ile
            100                 105                 110

His Pro Asn Arg His Thr His Thr Asp His His Ile Phe Phe Val Asn
        115                 120                 125

Lys Ala Tyr Leu Pro His Glu Thr Pro Glu Pro Leu Lys Met Tyr Arg
```

```
                130             135             140
Glu Lys Glu Leu Glu Lys Lys Arg Gly Asn Gly Arg Val Pro Lys
145                 150                 155                 160

Asn Trp Glu Asn Ile Tyr Asp Tyr Asp Val Tyr Asn Asp Ile Ser Asp
                165                 170                 175

Leu Asp Ser Asn Ser Thr Asn Lys Pro Pro Ile Leu Gly Gly Leu Val
            180                 185                 190

Pro Tyr Pro Arg Gly Arg Thr Gly Arg Pro Cys Leu Gln Asn Asp
        195                 200                 205

Asp Arg Tyr Glu Thr Arg Cys Ala Ile Lys Asp Val Tyr Val Pro Ser
    210                 215                 220

Asp Glu Arg Phe Ser Asp Leu Lys Lys Ser Asp Phe Asp Ile His Gly
225                 230                 235                 240

Leu Arg Ser Val Leu Arg Asp Ile Lys Asp Lys Leu Lys Ala Ser Leu
                245                 250                 255

Gly Lys Ser Pro Lys Arg Leu Glu Ser Leu Lys Asp Val Tyr Ala Ile
            260                 265                 270

Tyr Glu Pro Arg Ser Phe Phe Arg Arg Gly Lys Phe Pro Met Pro Gln
        275                 280                 285

Val Ile Glu Gly Asn Lys Ser Gly Trp Arg Thr Asp Glu Glu Phe Ala
    290                 295                 300

Arg Glu Met Leu Ala Gly Val Asn Pro Met Val Ile Arg Arg Leu Gln
305                 310                 315                 320

Ser Phe Pro Pro Thr Ser Asn Leu Asn Pro Ser Asp Tyr Gly Asp Gln
                325                 330                 335

Asn Ser Lys Ile Thr Pro Lys Gln Ile Met Asn Gly Met Glu Gly Leu
            340                 345                 350

Thr Val Asp Gln Ala Ile Ala Glu Asn Lys Leu Tyr Ile Leu Asp His
        355                 360                 365

His Asp Leu Ile Ile Pro Tyr Leu Lys Arg Ile Asn Thr Thr Ser Thr
    370                 375                 380

Lys Thr Tyr Ala Thr Arg Thr Leu Leu Phe Leu Lys Asn Asp Gly Thr
385                 390                 395                 400

Leu Lys Pro Leu Ala Ile Glu Leu Ser Leu Pro His Pro Gln Gly Tyr
                405                 410                 415

Gln Phe Gly Ala Ile Ser Lys Ile Leu Leu Pro Asp Lys Gly Lys Ile
            420                 425                 430

Gly Glu Pro Leu Trp Gln Leu Ala Lys Ala Tyr Val Val Val Asn Asp
        435                 440                 445

Ser Gly His His Gln Leu Ile Ser His Trp Leu Asn Thr His Ala Val
    450                 455                 460

Ile Glu Pro Phe Val Ile Ala Thr His Arg Gln Leu Ser Val Val His
465                 470                 475                 480

Pro Ile His Lys Leu Leu Val Pro His Phe Arg Tyr Thr Met Lys Ile
                485                 490                 495

Asn Ala Leu Ala Arg Ser Thr Leu Ile Asn Thr Asp Gly Ile Ile Glu
            500                 505                 510

Lys Thr Gln Tyr Pro Ser Lys Tyr Ser Met Glu Met Ser Ser Phe Ala
        515                 520                 525

Tyr Gln Asn Trp Asp Leu Thr Gln Gln Ala Leu Pro Ala Asp Leu Ile
    530                 535                 540

Lys Arg Gly Ile Ala Ile Glu Asp Pro Ser Ala Pro His Gly Leu Gln
545                 550                 555                 560
```

-continued

```
Leu Leu Ile Lys Asp Tyr Pro Tyr Ala Val Asp Gly Leu Asp Ile Trp
            565             570             575

Thr Ala Ile Lys Thr Trp Val Arg Glu Tyr Cys Ser Ile Tyr Tyr Lys
            580             585             590

Asn Asp Glu Met Ile Arg Asn Asp Pro Glu Leu Lys Ser Trp Trp Asn
        595             600             605

Glu Val Arg Glu Arg Gly His Glu Asp Lys Lys Asp Glu Pro Trp Trp
        610             615             620

Pro Lys Met Gln Ser Ile Glu Glu Leu Ile Asn Ser Cys Thr Ile Ile
625             630             635             640

Ile Trp Ile Ser Ser Ala Leu His Ala Ala Val Asn Phe Gly Gln Tyr
            645             650             655

Pro Tyr Gly Gly Phe Leu Pro Asn Arg Pro Ser Thr Ser Val Arg Phe
            660             665             670

Leu Pro Glu Glu Gly Thr Ser Glu Tyr Leu Glu Leu Gln Ser Asn Thr
        675             680             685

Asp Lys Ala Phe Leu Lys Thr Phe Thr Ser Glu Leu Gln Glu Asn Asp
        690             695             700

Leu Leu Asn Ile Thr Thr Ile Gln Leu Leu Ser Ser His Ser Leu Asp
705             710             715             720

Glu Ser Tyr Leu Gly Gln Arg Ser Asp Pro Asn Trp Thr Phe Asp Lys
            725             730             735

Asn Ala Leu Asp Ala Phe Glu Asn Phe Lys Arg Lys Leu Val Glu Ile
            740             745             750

Gly Glu Met Ile Gly Lys Arg Asn Lys Asp Asp Met Leu Lys Asn Arg
            755             760             765

Ala Gly Arg Glu Val Lys Met Thr Tyr Thr Leu Leu Leu Pro Thr Ser
770             775             780

Gln Pro Gly Ile Thr Cys Arg Gly Ile Pro Asn Ser Ile Ser Ile
785             790             795
```